United States Patent [19]

Coleman et al.

[11] Patent Number: 5,441,894
[45] Date of Patent: Aug. 15, 1995

[54] DEVICE CONTAINING A LIGHT ABSORBING ELEMENT FOR AUTOMATED CHEMILUMINESCENT IMMUNOASSAYS

[75] Inventors: Carole L. Coleman, Lindenhurst; Kevin R. Genger, Chicago; Hugh W. Graham, Waukegan; Charles F. Hanna; Omar S. Khalil, both of Libertyville; David C. Wender, Mundelein, all of Ill.

[73] Assignee: Abbott Laboratories, Abbott Park, Ill.

[21] Appl. No.: 56,219

[22] Filed: Apr. 30, 1993

[51] Int. Cl.⁶ ............................................ G01N 33/543
[52] U.S. Cl. .................................... 436/518; 422/55; 422/58; 422/102; 435/810; 436/164; 436/172; 436/527; 436/528; 436/533; 436/534; 436/805; 436/809; 436/810
[58] Field of Search ............... 436/518, 519, 527, 528, 436/533, 534, 805, 809, 810, 164, 169, 172; 422/50, 52, 55, 60, 56, 57, 58, 102; 435/810

[56] References Cited

U.S. PATENT DOCUMENTS

| | | | |
|---|---|---|---|
| 3,992,158 | 11/1976 | Przyblowicz et al. | 253/23 |
| 4,166,093 | 8/1979 | Smith-Lewis et al. | 422/56 |
| 4,363,874 | 12/1982 | Greenquist | 435/7 |
| 4,487,839 | 12/1984 | Kamentsky | 436/518 |
| 4,552,839 | 11/1985 | Gould et al. | 435/7 |
| 4,587,102 | 5/1986 | Nagatomo et al. | 422/56 |
| 4,632,901 | 12/1986 | Valkirs et al. | 435/5 |
| 4,632,910 | 12/1986 | Lee et al. | 501/97 |
| 4,652,533 | 3/1987 | Jolley | 436/518 |
| 4,857,652 | 8/1989 | Schaap | 549/510 |
| 4,931,223 | 6/1990 | Bronstein et al. | 252/700 |
| 4,931,569 | 6/1990 | Edwards et al. | 549/221 |
| 4,962,192 | 10/1990 | Schaap | 536/18.1 |
| 4,972,258 | 11/1990 | Wolf et al. | 358/93 |
| 4,978,614 | 12/1990 | Bronstein | 435/21 |
| 4,999,163 | 3/1991 | Lennon et al. | 422/58 |
| 5,004,565 | 4/1991 | Schaap | 252/700 |
| 5,006,309 | 4/1991 | Khalil et al. | 422/56 |
| 5,089,424 | 2/1992 | Khalil et al. | 436/518 |
| 5,135,719 | 8/1992 | Hillman et al. | 422/101 |
| 5,149,622 | 9/1992 | Brown et al. | 435/5 |
| 5,244,630 | 9/1993 | Khalil et al. | 422/52 |

FOREIGN PATENT DOCUMENTS

| | | | |
|---|---|---|---|
| 0106662 | 4/1984 | European Pat. Off. | G01N 21/03 |
| 0131934 | 1/1985 | European Pat. Off. | |
| 0200381 | 11/1986 | European Pat. Off. | |
| 0329120 | 8/1989 | European Pat. Off. | G01N 26/76 |

OTHER PUBLICATIONS

Khalil et al (1991) "Abbott Prism . . . " Clin Chem 37: 1540–1547.
Khalil et al (1991) "Reaction Tray and Noncontact . . . " Clin Chem 37: 1612–1617.
International Search Report for PCT/US94/04382 issued by European Patent Office on 17 Aug. 1994.

*Primary Examiner*—Toni R. Scheiner
*Assistant Examiner*—Christopher L. Chin
*Attorney, Agent, or Firm*—Mark C. Bach

[57] ABSTRACT

An improved device is used for performing solid-phase chemiluminescent immunoassays. The device comprises a container having a fibrous matrix and a porous absorbent material. An improvement in the device is the use of light absorbing material as the absorbent material or as a light barrier between the fibrous matrix and the absorbent material. A second improvement comprises a fibrous matrix of binderless fiber matrix, such as glass fiber. The invention improves the direct measurement of the chemiluminescent signal from a solid surface by reducing background signal. The device is disposable and is suitable for manual use or for use with an apparatus having programmed instructions. The device is designed to be employed in a variety of solid-phase diagnostic assays such as sandwich or competitive binding assays. The device is also designed for use with microparticle capture or ion capture methods of separating the immunochemical reaction products.

11 Claims, 7 Drawing Sheets

DEVICE CONTAINING A LIGHT ABSORBING ELEMENT FOR AUTOMATED CHEMILUMINESCENT IMMUNOASSAYS

BACKGROUND OF THE INVENTION

The present invention is directed toward an improved device for use in chemiluminescent immunoassays (CLIA). In particular, the present invention improves the direct measurement of a chemiluminescent signal from a solid surface. The present invention relates to an apparatus for use in heterogeneous immunoassay wherein a chemiluminescent signal provided by the immobilized product of an immunochemical reaction from a porous matrix is measured. The improvement relates to the reduction of background chemiluminescent signals which improves the sensitivity, precision and accuracy of chemiluminescent assays.

Techniques for performing an immunoassay are generally known in the art. For example, conventional enzyme immunoassay procedures involve a series of steps wherein an analyte in a sample material is initially bound to a corresponding antigen or antibody reagent. A second antigen or antibody is then introduced into the sample which has been labeled with an enzyme or other substance capable of being detected directly or after addition of a suitable reagent such as a chromogenic or fluorogenic substrate or a trigger solution for activating chemiluminescence. The generated signal is then read to indicate the absence or presence of the antigen or the antibody in the sample.

Solid phase immunoassay procedures are preferred over other diagnostic methods because of their specificity and sensitivity as interfering substances can be washed away before optical readout.

One form of a conventional solid-phase immunoassay is a "sandwich assay" which involves contacting a test sample suspected of containing an antibody or antigen with a material which has attached to it a protein or another substance capable of binding the antigen or the antibody to the surface of the support. After the antibody or antigen is bound to the support material it is treated with a second antigen or antibody, which is conjugated with an enzyme, a fluorophore or a chemiluminescent label. The second antigen or antibody then becomes bound to the corresponding antibody or antigen on the support. Following one or more washing steps to remove any unbound material in an enzyme immunoassay, an indicator substance, for example, a chromogenic substrate, is added which reacts with the enzyme to produce a color change. The color change can be observed visually or more preferably by an instrument to indicate the presence or absence of the antibody or antigen in the sample. For solid-phase fluorescence or chemiluminescence immunoassays, fluorescent labeled moieties can be monitored by using excitation at an appropriate wavelength, while chemiluminescent labeled antigens or antibodies can be followed after reaction by chemically activating the chemiluminescent labels to generate light which can be detected by photometric means.

Many procedures and apparatuses have been designed to perform solid-phase immunoassays. U.S. Pat. No. 4,632,910 discloses an apparatus having a porous filter containing a bound receptor for complexing an analyte. In this apparatus an absorbent material is positioned below the porous filter to assist the fluid sample in flowing through the filter. A labeled antibody is then added to the porous filter to detect the presence or absence of the analyte. This approach leads to assays with limited sensitivities as the sample and conjugate incubation takes place on the same matrix. Non-specific binding of the sample and conjugate to the porous matrix can occur and contribute to the background of the assay and limit its sensitivity.

In another approach, European Patent Application No. 0131934 discloses an assay device having a plurality of aligned adjacent incubation wells located on its top surface which empty through a filter membrane located above a waste reservoir. U.S. Pat. No. 4,652,533 discloses an assay method using such a device. A solid-phase fluorescent immunoassay reaction mixture is placed in the well and drawn through the membrane by applying reduced pressure to the waste reservoir to separate a solid-phase reaction product from a liquid-phase reactants so that the solid-phase reaction product can be observed. This approach, however, has serious limitations. First, it is limited to use of microparticles as a capture phase. Second, the sample, conjugate and microparticles are incubated in the same incubation well that the optical reading takes place. Non-specific binding of sample and conjugate, labeled antigen or antibody, to the membrane filter in the reading well and the wall of the well can occur and contribute to the background of the assay and limiting assay sensitivity. Third, because of using a common vacuum manifold to a plurality of filters, a pinhole in one of the wells will lead to air leaking through this well and no filtration for other wells in the disposable reaction tray. Fourth, such a disposable device cannot be used for chemiluminescence immunoassay measurements where extreme light tight conditions around each well are required. Other microparticle based vacuum filtration devices for immunoassays are available commercially such as Millititer ® Plate from Millipore Corporation, Bedford, Mass.

U.S. Pat. Nos. 5,006,309 and 5,244,630, both incorporated herein by reference, disclose devices having an incubation well and read well with a porous matrix and means positioned below the porous matrix to enhance the flow of sample and assay reaction mixtures through the porous matrix. The assay reagents are incubated in the incubation well and then transferred to the read well where capture reagent/analyte complexes are immobilized on the matrix.

U.S. Pat. No. 5,089,424 and U.S. patent application Ser. No. 630,344 (filed Dec. 17, 1990), now abandoned both incorporated herein by reference, disclose devices and methods for performing chemiluminescent assays using microparticles and ion capture methods.

Other methods for performing solid-phase immunoassays are disclosed in U.S. Pat. Nos. 4,587,102, and 4,552,839, and European Patent Application 0200381. These references generally disclose procedures for employing particles having a receptor to bind an analyte which is subsequently labeled and deposited on a matrix or other support system. The particle complex is treated with an indicator substance to indicate the presence or absence of an analyte.

While many immunoassay procedures and devices have proved useful, better procedures and devices are continually being sought to improve reliability, efficiency and sensitivity. The present invention provides all of these improvements.

SUMMARY OF THE INVENTION

The present invention is directed toward an improved device suitable for performing solid-phase diagnostic assays. The improved device is particularly advantageous when used in conjunction with solid-phase diagnostic assays that utilize chemiluminescent or luminescent labels. The device of the present invention comprises at least one read well, wherein the well retains and immobilizes a specific binding pair complex and in which the results of the reaction can be read. The read well has an entrance port and a means for holding a quantity of sample and reagent mixtures positioned over a fibrous matrix which is porous and retains and immobilizes immune complexes formed in such mixtures. The read well further comprises a fluid removal means positioned below the fibrous matrix to enhance the flow of sample and assay reaction mixtures through the fibrous matrix. A preferred means of fluid removal is the use of an absorbant pad in intimate contact with the fibrous matrix. An improvement in the device comprises a light absorbing means such that the light generated in the fluid removal means is substantially reduced compared to a white absorbant pad. Preferably, the light absorbing means is an absorbant pad black in color. An additional improvement in the device comprises a fibrous matrix formed without the use of binder material.

"Specific binding pair complex" as used herein means two different molecules (specific binding members) where one of the molecules through chemical or physical means specifically binds to the second molecule, such as an antibody or other binding protein bound to an antigen. Such complexes include hapten-anti-hapten complexes such as biotin-anti-biotin, avidino-biotin, carbohydrate-lectin, complementary nucleotide sequences, effector-receptor, enzyme cofactor-enzyme, enzyme inhibitor-enzyme, and the like. It will be appreciated that one skilled in the art can conceive of many other specific binding pair complexes and methods of use to which the present inventive concepts can be applied.

The reaction product of the sample and reagent mixtures is immobilized by the fibrous matrix as a result of an interactive property between the fibrous matrix and the reaction product, such as through particulate reactants or through hydrophilic-hydrophilic binding interaction, ionic binding interactions, and the like. The fibrous matrix is porous material preferably composed of fibers having an average spatial separation greater than about 3 microns. Separation of the immune complex on the fibrous matrix can be affected by using latex microparticles with antibodies or antigens immobilized on its surface as the capturing solid phase and separating them from the reaction mixture by their physical adhesion to the fibrous matrix. Microparticles used in this process may have diameters larger or smaller than the spatial separation between the fibers of the matrix, but in any case, the fluid flow through the fibrous matrix must not become restricted by the particles.

Another preferred method of separation is that which is described in U.S. patent application Ser. No. 150,278 (filed Jan. 29, 1988) now abandoned and U.S. patent application Ser. No. 375,029 (filed Jul. 7, 1989 now abandoned), both of which are incorporated herein by reference, directed to the use of ion capture separation wherein the fiber matrix is treated with a cationic detergent to render the fibers positively charged. The antibody, or antigen, for the assay in question is chemically attached to a polyanionic acid such as polyglutamic acid or polyacrylic acid. Separation of the immunochemical reaction product will be affected by the electrostatic interaction between the positively charged matrix and the negatively charged polyanion/immune complex.

A preferred device further incorporates an incubation well. A sample can be incubated with reagents to form a reaction mixture in the incubation well. The reaction mixture is transferred from the incubation well into the read well by a non-contact means using jets of fluid to move the reactants between the two wells. This preferred device preferably has surface features surrounding each well pair that mates with a chemiluminescent reader head in such a way that a light-tight seal is created to allow low-light level measurements. More preferably, associated with each incubation well/read well pair in the disposable device is a hole to vent the air originally entrapped in the absorbant pad and is displaced by the reaction mixture and wash solutions.

The present improved device can be used in various methods for performing solid-phase assays in the device using either microparticle or ion capture separation techniques. The term "capture agent" will be used to describe microparticles coated with an immunochemical reactant or a polyanion attached to an immunochemical reactant. In the former case the fibrous matrix may be treated with substances that facilitate adherence of the microparticles and flow of the remaining fluids. In the latter case the fibrous matrix will be treated with cationic materials that facilitate attachment of the polyanion-immunoreactant complex to the matrix. The device can be employed to conduct sandwich or competitive assays.

DETAILED DESCRIPTION OF THE INVENTION

The present invention is directed toward an improved device for performing a solid-phase chemiluminescent immunoassay and methods for performing solid phase immunoassays with this device. The device is disposable and is suitable for manual use or for use with an apparatus having programmed instructions and means for adding sample and reagents, injecting a wash solution to transfer an assay reaction mixture to a read well and for optically reading the results of the assay.

The device is designed to be employed in a variety of solid-phase diagnostic assay formats such as sandwich or competitive binding assays. The device is also designed so that it can be used for fluorescence or colorimetric detection methods. In addition, a special feature is preferably designed into this device to allow light tight seal for chemiluminescence measurements. Further the device of the present invention can be used for separating the immunochemical reaction products by immobilizing the products on a fibrous matrix through an interactive property between the fibrous matrix and the reaction product, such as through particulate reactants (microparticle capture methods) or through hydrophilic-hydrophilic binding interaction, ionic binding interactions, and the like (ion capture methods).

Samples which can be assayed by the device include biological fluids such as whole blood, spinal fluid, urine, serum, and plasma. It is also envisioned that other fluid samples of a non-biological nature can be analyzed using the disposable device.

The device is preferably molded to have sets of wells, each set comprises a shallow incubation well for receiving a sample which communicates through a sloping passage means with a read well for detecting the results of the assay procedure. Preferably, the device is molded of opaque polystyrene, acrylonitrile-butadiene-styrene ter-polymer (ABS), polycarbonate, polyacrylates, high impact polystyrene or some other moldable material which is inert to the assay components. The sample is placed either manually or mechanically into the shallow incubation well and reacted (hereinafter described) and after an appropriate time transferred and washed into the read well where the results of the assay are monitored or detected.

Figure 1:
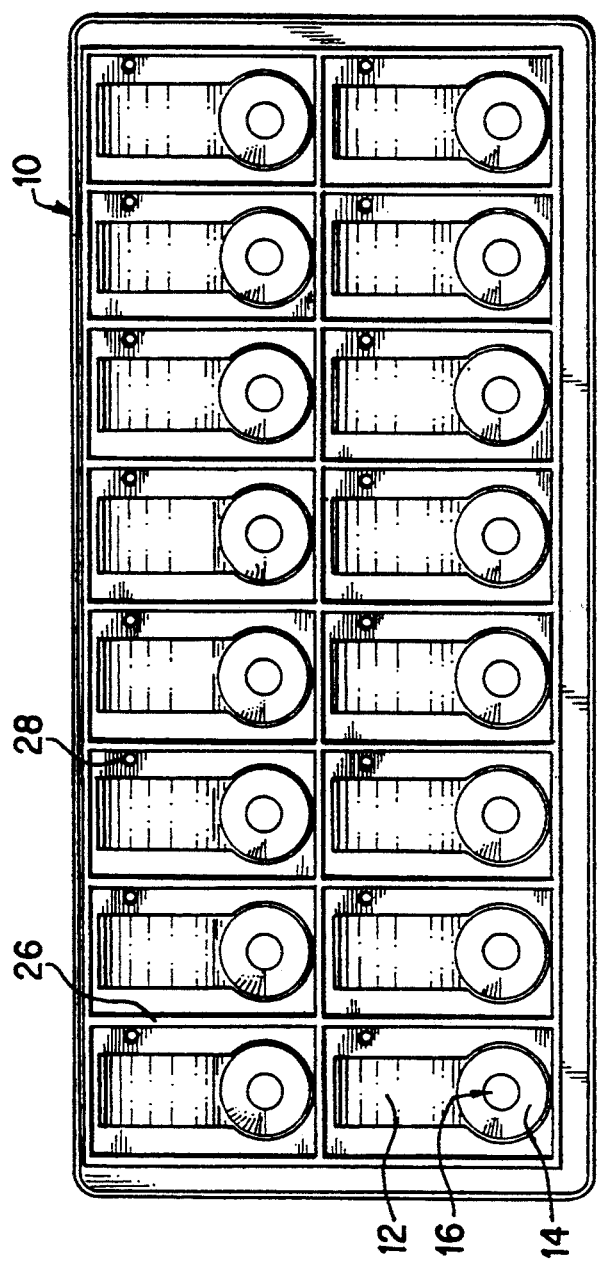
FIG. 1 is a top plane view for one embodiment of the diagnostic device.
Figure 2:
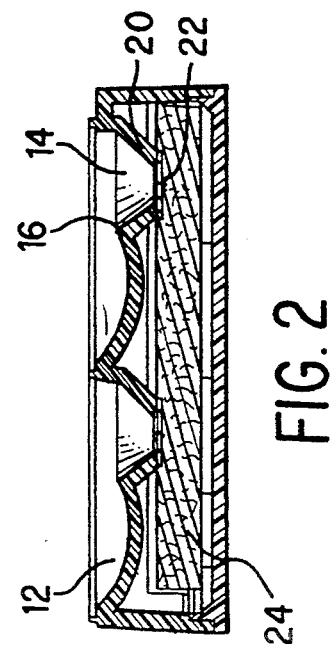
FIG. 2 is a side view and cross section of the diagnostic device 10 of FIG. 1 cut along the short axis.
Figure 3:
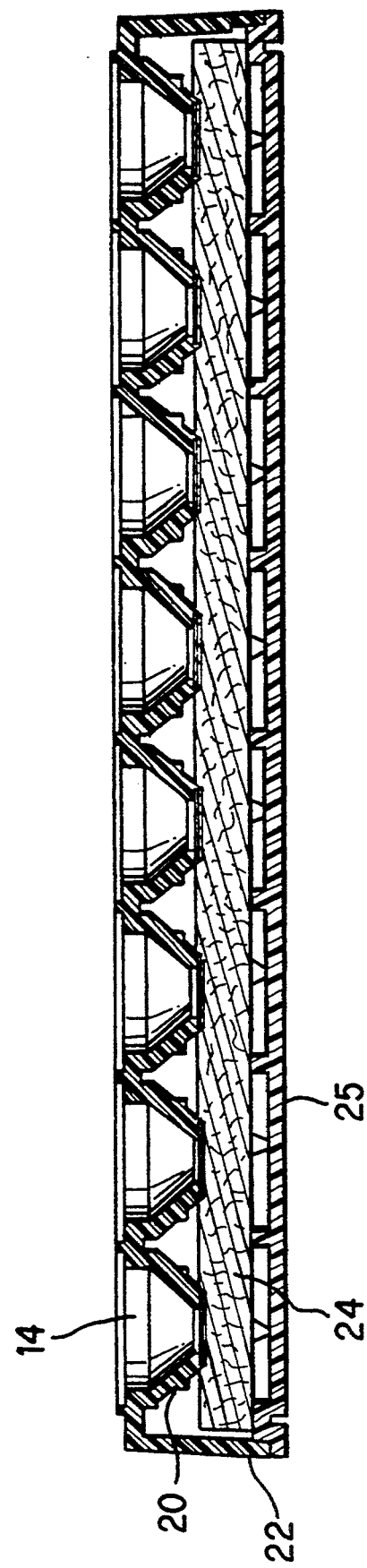
FIG. 3 is a side view and cross section of the diagnostic device 10 of FIG. 1 cut along the long axis.

In one preferred embodiment of the present invention is the device 10 shown in FIGS. 1 and 2, having a plurality of the shallow incubation wells 12, passage means 16 corresponding read wells 14. Each read well 14 has a holding means 20, a fibrous material 22 assembled into a square or a rectangular array. Each read well element has a separate fibrous matrix 22 and either a separate absorbent material element 24 or a common absorbent material pad or layers of absorbent material pads. It can also be assembled in such a way that individual absorbent material elements 24 are in intimate contact with the fibrous matrix 22 on one end and with a common absorbent layer on the other end. Any of the absorbant material configurations is chosen to enhance diffusion of fluids away from the fibrous matrix 22. For high throughput instruments, the array assembly is preferred. The surface feature 26 is an array of rectangular ribs wherein each rectangle encloses an incubation well/read Well pair and acts as a light seal when a chemiluminescence detector, with matching groove padded with compressible polymeric material, mates with it. Vent hole 28 is associated with each incubation well/read well pair. It vents out the air originally entrapped in the absorbant pad and is displaced by reaction mixture and transfer and wash solutions. Intimate contact between the fibrous matrix 22 and the absorbent material 24 is assured by compressing the absorbent material against the fibrous matrix using surface features 25 on the internal bottom surface of the disposable device 10.

Shallow incubation well 12 can be semi-spherical, semi-cylindrical, toroidal or any complex curvature with no sharp corners. The largest radius of curvature of the shallow incubation well is along the axis connecting the incubation well to the read well. Dimensions of the shallow Incubation well 12 are chosen to maximize the volume of reaction mixture that can be incubated in the well, without having a steep fluid angle. A high fluid exit angle requires high wash solution injection speeds. Under these conditions fluids from incubation wells may overshoot the read well as they are transferred. On the other hand low exit angles may lead to self transfer or spilling of reaction mixture into the read well. Choice of dimensions and their relationship to fluid properties can be easily calculated by those skilled in the art.

Figure 4:
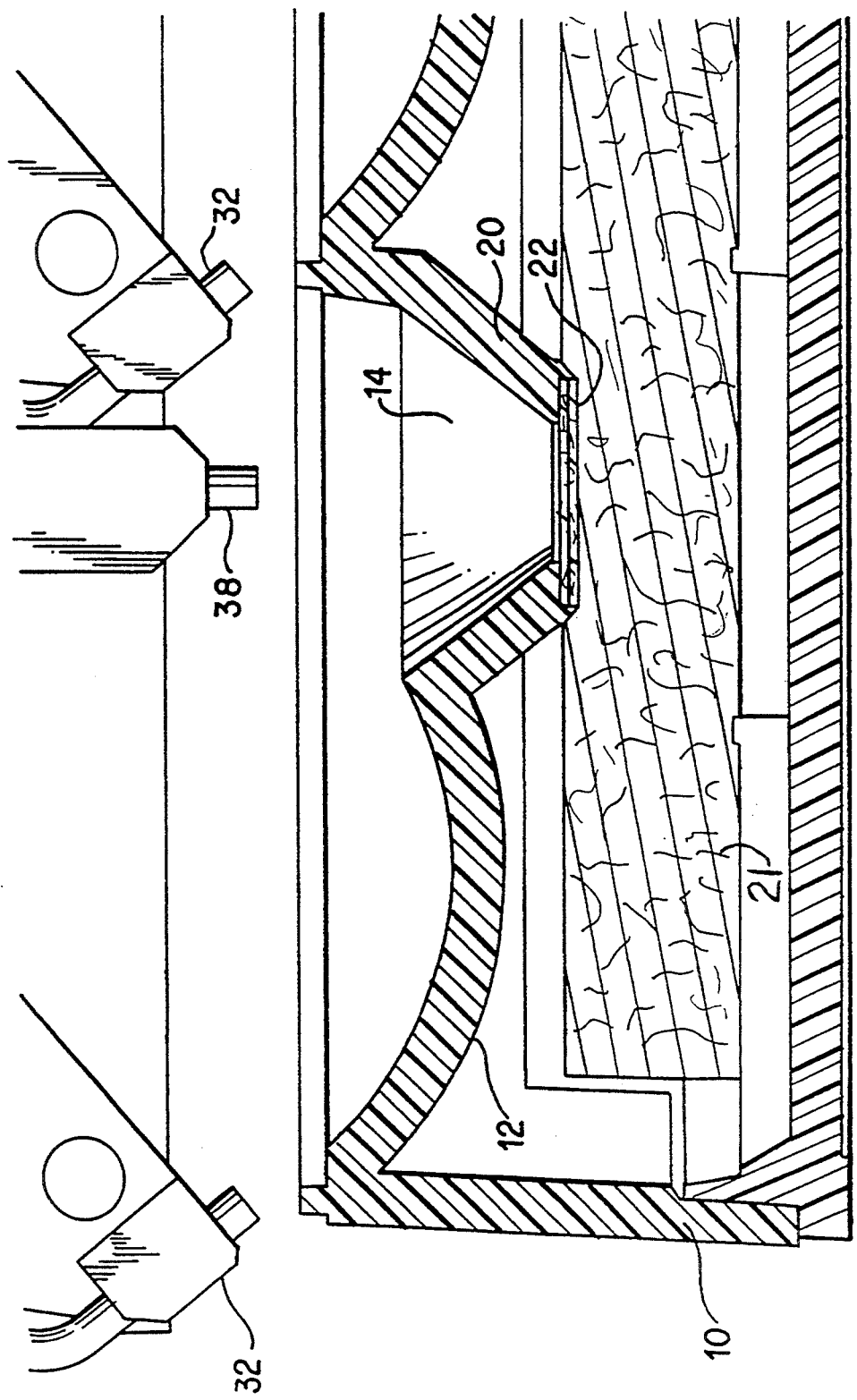
FIG. 4 shows a side view and cross section of a single well pair of diagnostic device 10 positioned for transfer under device 30.
Figure 4A:
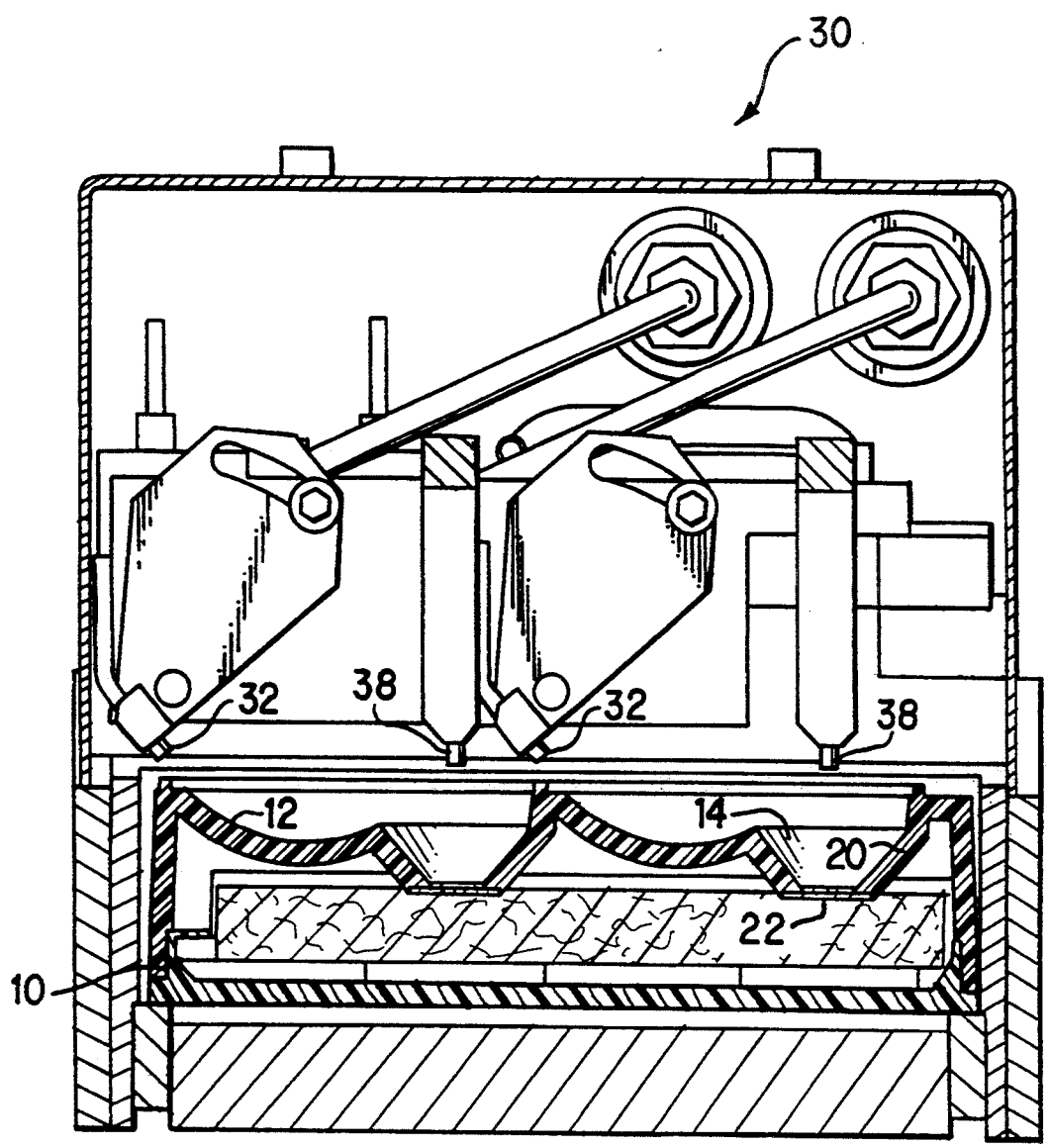
FIG. 4a shows a side view and cross section of diagnostic device 10 positioned for transfer under device 30.
Figure 5A:
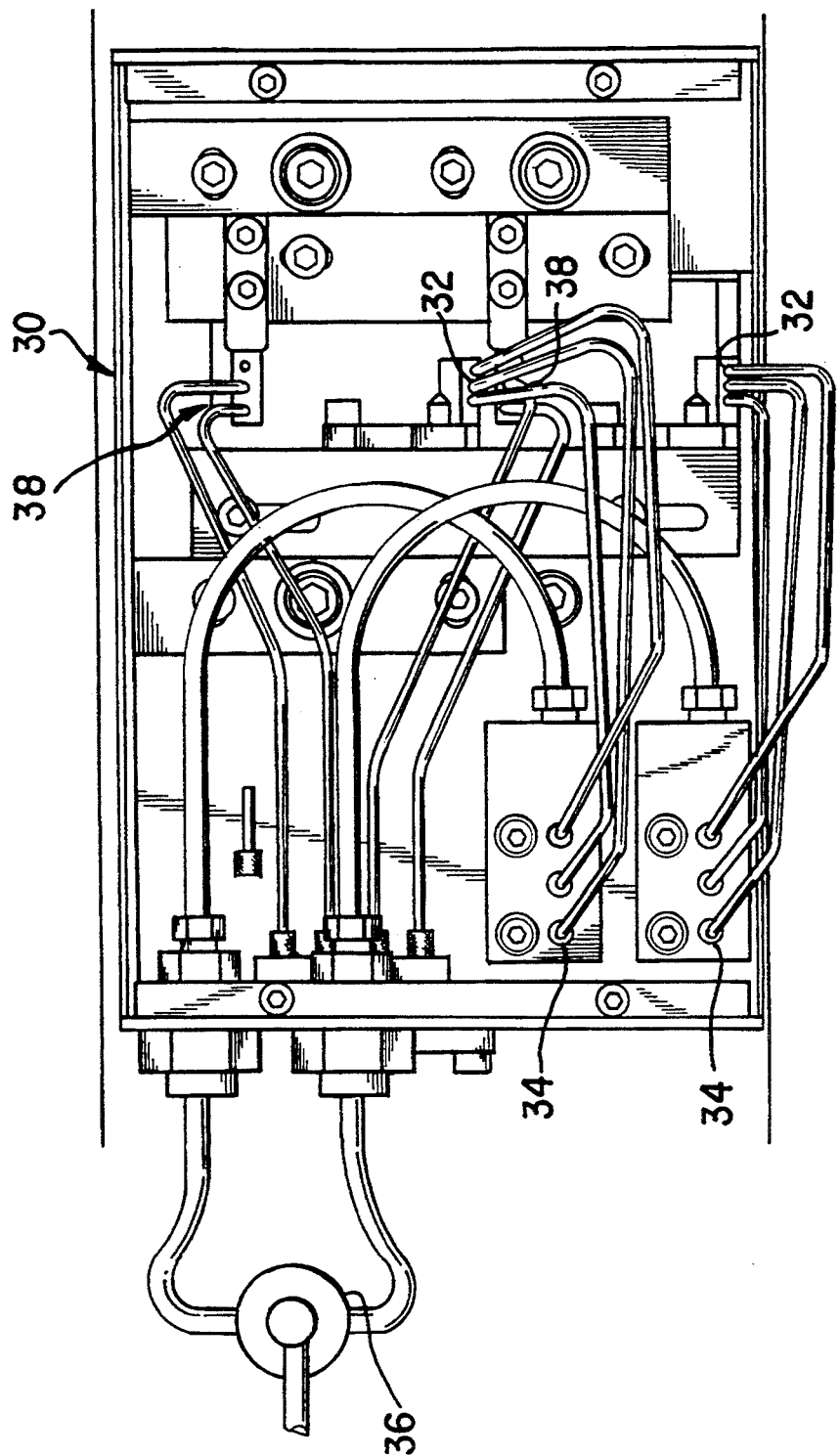
FIG. 5a shows an expanded top view of the device 30.
Figure 5B:
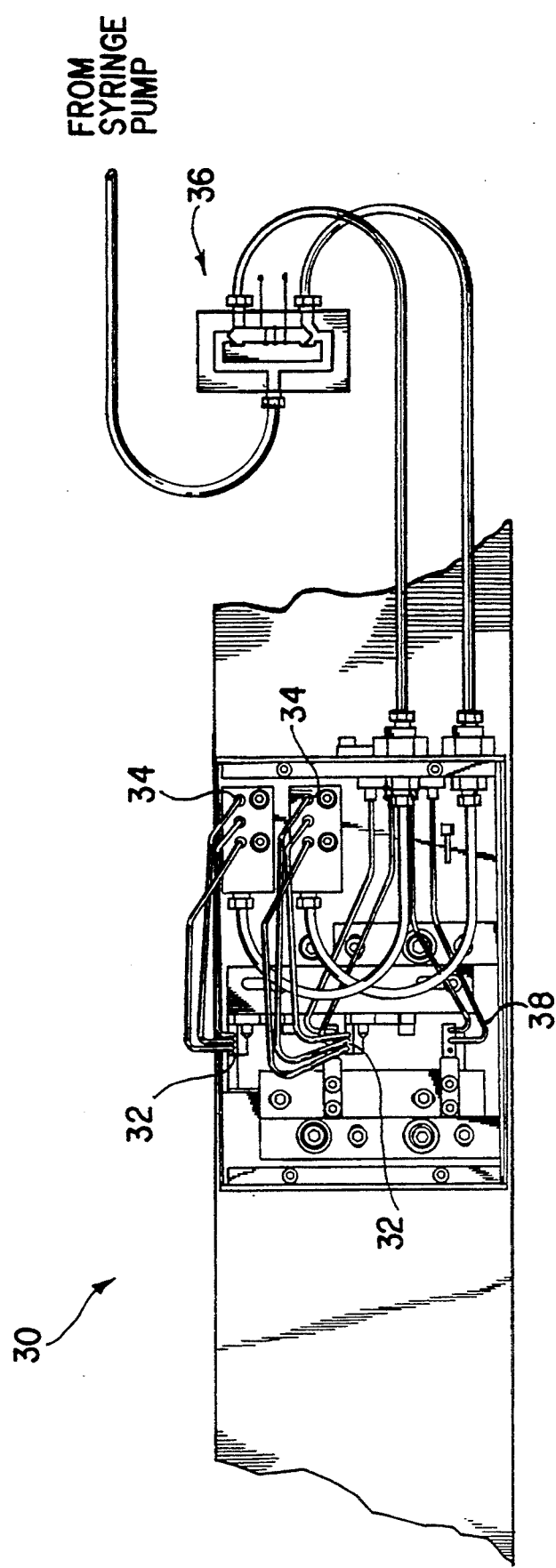
FIG. 5b shows a top view of the device 30.
Figure 6:
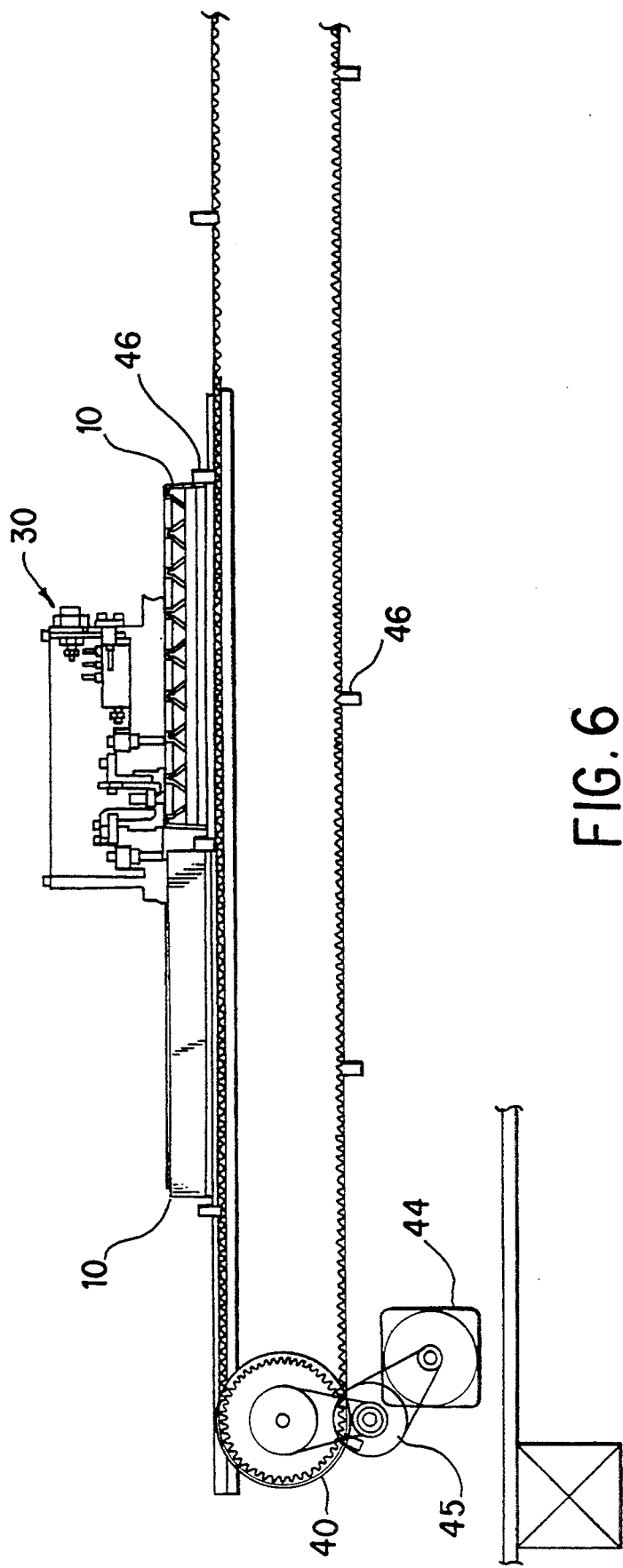
FIG. 6 shows the transport mechanism for moving device 10 under the transfer device 30.

Transfer takes place by injecting wash fluid at the side of the shallow incubation well 12, farthest from the read well 14 using a transfer device 30 shown in FIG. 4. A group of nozzles 32 are positioned close to the surface of each incubation well 12 to inject transfer or wash solutions. Said solutions are injected into the shallow incubation well 12 at a small angle to the tangent to the surface of the well at its region of intersection with the meniscus of the reaction mixture. Angle between direction of solution injection and tangent to shallow incubation well surface are generally kept below 45°. Angles between 5° and 20° are preferred.

Transfer solution injection volumes and speeds at which it is injected into the shallow incubation well 12 depend on the reaction mixture volume needed to be transferred. Slow transfer solution injection speeds into the shallow incubation well 12 may lead to a partial transfer and successive dilution of reaction mixture. Then larger transfer solution volumes will be required to complete the transfer, which in turn necessitates a larger capacity of absorbent material 24 and hence a larger size disposable. Alternatively, the use of high transfer solution injection speeds may cause the reaction mixture to overshoot read well 14 and may cause the reaction mixture to splash back towards the injectors and contaminate them. In other words, depth and curvature of shallow incubation well 12, angle of exit port 16 and volume and injection speed of wash solution are dependent on the total assay volume to be incubated in well 12. Total assay volume in turn is optimized to achieve the desired binding reaction under the constraints of assay conditions. Those who are skilled in the art of fluid dynamics can calculate and optimize these dimensions once the essence of this invention is understood.

The read well 14 generally comprises a sloping down entrance port and holding means 20, a fibrous matrix 22, and an absorbent material 24. The entrance port and holding means 20 can be a molded portion of the device and preferably constitute a funnel-like structure which is an integral part of the incubation well 14. The holding means 20 is designed with sloping sides which contact the upper surface of the fibrous matrix 22 and is sized to hold a sufficient amount of sample, conjugate material or other reagents to satisfy the requirements of the particular assay being performed. The holding means 20 should be sufficiently opaque, preferably made of black plastic material, to decrease background interference with the optics system.

Each pair of incubation and read wells is preferably surrounded by a raised portion, preferably in the form of a rib or a thin plastic wall 26 which is a molded feature of the disposable device and acts as a mating part for another feature on a chemiluminescence reader to create a light tight seal. The height of such light seal is preferably between about 0.020 and about 0.10 inches, and more preferably between about 0.04 and about 0.08 inches.

In a preferred embodiment of this invention, the transfer device 30 comprises two groups of nozzles 32. Each group of nozzles is directed towards an incubation well of the reaction tray 10 that has two rows of incubation well/read well pairs. Each group of nozzles is connected to fluid distribution manifold 34 into which transfer or wash solutions are injected via a stepper motor controlled pump. The first set of nozzles is directed towards the first incubation well of the plurality of well pairs and the second set of nozzles is directed into the second parallel incubation well and fluid flow is diverted to the second set of nozzles via a valve 36 using the same pump. Alternatively, an independent pump can be used for each set of nozzles. Thus the transfer process can be performed on two parallel incubation wells either sequentially or simultaneously. A single pulse or several pulses of transfer solution are injected into the incubation well with a delay time between injections to allow the transferred fluids to drain from the read well 14. This prevents splashing and back washing of the reaction mixture from the read well into the incubation well, an action that can reduce transfer efficiency. Drainage time between fluid transfers is preferably within the range of about 2 to about 180 seconds, more preferably between about 2 to about 60 seconds and most preferably between about 2 to about 15 seconds. After the transfer of the reaction mixture, wash solution may be injected into the incubation well in a manner similar to the transfer solution to wash any capture agent analyte/conjugate complex on the walls of the retaining means 20 into the fibrous matrix 22 or to wash the unretained portions of the reaction mixture from the fibrous matrix 22.

Alternatively, in the same transfer device and located on top of the parallel read wells 14 is another set of nozzles 38; each nozzle is connected to a pump either directly or via a valve and can be used to deliver a reagent to the transferred and washed reaction mixture on the fibrous matrix 22. One such nozzle can be used for adding additional wash solution into the read well to transfer any capture agent analyte/conjugate complex on the walls of the retaining means 20 into the fibrous matrix 22 where it is retained and immobilized. This in turn decreases fluctuations in assay numbers due to varied amounts of retained immune complex. The same nozzle can be used to wet the fibrous matrix with wash solution before transfer to improve fluid flow into the matrix and the absorbent material. Another nozzle can be used for adding a second reagent to the transferred reaction mixture on the fibrous matrix 22.

The transfer and wash solutions preferably contain a small amount of detergent in order to decrease the surface tension and improve wetting the plastic and facilitate transfer. Detergents such as Tween®, sodium dodecyl sulfate or lithium dodecyl sulfate can be used for this purpose. Other surface active agents can be contemplated and used by those skilled in the art.

An alternate way to transfer reaction mixture from shallow incubation well 12 into read well 14 is to use a combination of air and wash solution nozzles. For example, alternating wash solution nozzles and compressed air nozzles in a group of nozzles directed towards the wall of each shallow incubation well 12 and simultaneously activating them can affect the same transfer described previously. This saves in the fluid volume used in the assay and hence in the volume of fluids to be disposed of in the absorbent material 24.

The transfer device 30 can be moved by robotic means and accurately positioned on subsequent incubation wells to affect transfer and wash of the reaction mixture. A preferred way to bring new wells under the transfer device 30 is to move the disposable device 10 in a controlled manner under the transfer device 30 using a mechanism 40, comprised of a timing belt 42 controlled by a stepper motor 44 and gear reduction system 45. A rectangular plastic lug 46 pushes the disposable device 10 to new positions. Other means of moving the disposable device such as the use of linear actuators, metal belts or screw drives can be contemplated and used by those skilled in the art.

The fibrous matrix 22 is a thin disk-like porous material positioned below the entrance port and holding means 20 to retain and immobilize a complex from which an assay signal can be read. The phrase "retain and immobilize" means that the captured/labeled immune complexes while upon the fibers of the material are not capable of substantial movement to positions elsewhere within the material, (i.e., to other fibers), and cannot be readily removed completely from the material.

The pore size, particle retention size or spatial separation of the fibers comprising the fibrous matrix 22 is essential to the overall performance of the solid-phase immunoassay contemplated by the present invention. It must allow adequate void areas to assure the proper flow of reagents and sample through the fibrous matrix. Preferably, the spatial separation of the fibers must be larger than the diameter of the microparticles employed in a microparticle capture assay such that after the microparticles are deposited on the fibrous matrix, the matrix is not blocked but instead remains porous. As used herein "porous" means that the matrix is and remains a material into which fluids can flow and can easily pass through without the need to apply vacuum or pressure to facilitate its flow.

Alternatively, the fibrous matrix 22 may simply retain or filter a complex from which an assay signal can be read. Preferably, when the spatial separation of the fibers are smaller than the diameter of the microparticles employed in a microparticle capture assay, the quantity of microparticles deposited on the fibrous matrix must be controlled such that the matrix is not blocked but instead remains porous.

The fibrous material of the present invention can be chosen from any of a variety of porous materials such as glass, cellulose, nylon or other natural or synthetic fibrous material well known to those skilled in the art. A suitable material is H&V Product No. HC411 glass fiber filter paper, which has a nominal thickness of 0.055 inches, a mean pore size determined by the bubble point method of 4.1 microns with a particle retention size filtration range of about 2.6 to about 11 microns and a 98% capture efficiency for latex microparticles having a diameter of 1.2 microns (commercially available from Hollingsworth and Vose Co., West Groton, Mass.). The "particle retention size" of a depth filter refers to the size of particle that a particular grade of filter will effectively retain. There is no fixed relationship between the particle retention size of a porous material and the pore size of a porous material. However, the particle retention size is affected by the thickness of the material. The thickness of the porous material is a matter of choice largely based upon the properties of the sample being assayed, such as fluidity. Once a particular particle size is selected, the porous material of the present device would be selected according to the particle retention size and the fluid properties of the sample. Preferably, the porous material of the present device will retain the particles near the top surface of the porous material without substantially affecting the flow rate of the reaction mixture through the porous material into the absorbent material.

The fibrous matrix 22 is positioned against the holding means 20 and above a means that functions to facilitate the transportation of fluid through the fibrous matrix. This can be a reservoir means to which reduced pressure is applied during or after the transfer; or an absorbent element made of any moisture or fluid-retaining material which effectively retains fluid passing through the fibrous matrix 22. A preferred embodiment of this invention is that an absorbent material 24 is positioned below the fibrous matrix 22 and is in intimate contact with the lower surface of fibrous matrix 22 in order to absorb any reagent that flows through the fibrous matrix. This contact assures rapid transportation of the reaction fluids through the fibrous matrix 22.

The microparticles employed to perform the solid-phase immunoassay are selected to have an average size that is preferably small enough such that they are suspendable in water or a sucrose solution to facilitate their coating with an antibody or antigen. The average individual size of the microparticles, which is small enough to both be suspendable in solution and retained and immobilized in the fibrous matrix, is from about 0.1 to about 50 microns, more preferably from about 1 to about 10 microns in diameter. The microparticles can be selected from any suitable type of particulate material such as polystyrene, polymethylacrylate, polypropylene, latex, polytetrafluoroethylene, polyacrylonitrile, polycarbonate or similar materials.

Uncoated microparticles can be employed for binding some analytes but in many situations the particles are coated with a substance for binding an analyte, e.g., antibody or antigen, or a combination thereof.

The transfer and treatment of a sample with reagents in the device is preferably but not necessarily accomplished by automated means under computer control. Robotic arms can supply the necessary reagents by various transferring means communicating with reagent containers located external to the device and associated mechanisms. Most importantly an instrument mechanism or robotic means can position a pipetting or jet means for directing a stream of wash solution into the shallow incubation well 12.

Alternatively the assay device 10 can be placed on a conveyor where a timing belt can move it at precise time intervals to locations under automated pipettors, reagent dispensers, transfer devices, washing devices or detectors. Whether a linear or circular motion is used to move the disposable, it is ultimately brought under a transfer device which successively injects transfer fluid into well 12 to wash the assay reaction mixture through passage means 16, into the read well 14. This particular feature of the device 10 prevents contamination of the automated apparatus or pipetting means as well as the assay reaction mixture. Also, a pipette never needs to be washed to prevent cross contamination of other assays.

For illustration purposes the following procedures are provided:

In one form of a sandwich assay method a sample is added to the shallow incubation well and the device is placed on a transport means designed to hold a plurality of devices. Steps (a) through (e) may be performed by a microprocessor-controlled automated instrument or manually as follows:

(a) an analyte-specific conjugate is added to the shallow well containing a sample to form a mixture which is incubated for a sufficient time to allow any analyte present to complex with the analyte specific conjugate;

(b) microparticles are added to the mixture to form a microparticles analyte/conjugate complex; alternatively, the analyte/conjugate complex can be washed into the read well to which microparticles have been previously or simultaneously added;

(c) the incubated microparticles analyte/conjugate complex is washed into the receiving port of the read well and washed with a suitable buffer or water to transport the complex into the fibrous matrix;

(d) an indicator substance capable of producing a color change or other detectable signal in the presence of the microparticle analyte/conjugate complex is added to the read well; and (e) the assay signal is detected by optical means as a function of the presence or amount of analyte in the sample.

In a variation on the above procedure, steps (a) and (b), i.e., formation of analyte/conjugate complex and formation of microparticle analyte/conjugate complex, respectively, can be performed simultaneously by adding the capture agent, sample and analyte-specific conjugate to the shallow incubation well and incubated. The complex is then washed into the read well.

In the final step (e), detection of the signal produced in the read well varies with the type of label used. Thus for an enzyme labeled antigens or antibodies, a substrate solution is added in the read well and the product formed is detected by color development or generation of a fluorescent signal. For fluorophore labeled antigen or antibodies, direct excitation of fluorophore and detection of spontaneous or time resolved fluorescence signal is used. In the case of chemiluminescent labeled antigens or antibodies, detection is achieved by chemically activating the luminescent label and monitoring generated light. In all these methods of detection, either the total integrated signal over a period of time or the rate of change of signal over the observation period can be used to establish a standard curve for the assay and determine the concentration of analyte in unknown samples.

In another version of a solid-phase sandwich assay procedure the automated or manual steps can be performed as follows:

(a) a sample and capture agent are mixed together in the incubation well to form a complex of the microparticle and analyte;

(b) the microparticle analyte complex is treated with an analyte specific conjugate and incubated to form a microparticle analyte/conjugate complex (alternatively steps (a) and (b) can be performed simultaneously by adding sample, capture agent and an analyte specific conjugate to the incubation well and incubating);

(c) the complex is then transported into the read well by applying a wash of a suitable buffer or water through injector means;

(d) an indicator substance capable of producing a signal in the presence of the microparticle analyte/conjugate complex is added to the read well to form an assay signal;

(e) the assay signal is detected by optical means as a function of the presence or amount of analyte in the sample.

In the above procedure, the transportation step (c) can be performed either before or after the addition of the analyte specific conjugate to the microparticle analyte complex, i.e., either the microparticle analyte complex is transferred and then the analyte specific conjugate is added to the read well, or the analyte specific conjugate is added to the microparticle and analyte mixture in the incubation well and the resulting microparticle analyte/conjugate complex is then transferred to the read well.

In yet another solid-phase immunoassay approach the disposable device can be employed to perform a competitive binding assay. The automated or manual steps are as follows:

(a) a sample is added to a known amount of labeled antigen and capture agent capable of binding a suspect antigen to form a mixture in a incubation well;

(b) the mixture is washed into the read well where the capture agent becomes bound to the fibrous matrix;

(c) the fibrous matrix is washed to remove unbound antigen;

(d) an indicator substance is added to the read well to form an assay signal in the presence of the labeled antigen; and (e) the assay signal is detected by optical means as a function of the presence or amount of analyte in the sample.

It should be apparent that many variations of the above steps can be designed to form the microparticle analyte/conjugate complex which can be detected by optical means on the fibrous matrix. Generally the sandwich or competitive assay procedure and the choice of an analyte specific conjugate, and indicator substance are known to those skilled in the art and therefor are not discussed in great detail here. Instead, the present invention is directed toward the device described above and the method of transfer, and in a preferred embodiment to the device which is suitable for the automated performance of a solid-phase immunoassay process on a microprocessor-controlled automated instrument.

This method of incubation in one compartment, fluid transfer, separation and signal generation in another compartment described in this invention is not limited to microparticle based immunoassays. Thus another preferred embodiment of the invention is to use an ion capture separation method as described above. The different procedures and examples described above for the use of microparticles as a capture phase can be used with ion capture, where a polyanionic material attached to a hapten, antigen or antibody is used as a capture agent in place of the microparticles in each example. After transfer of the polyanionic material to the positively charged glass fiber matrix, the immune complex is retained and immobilized on the glass fiber matrix by ionic forces.

Competitive binding ion capture immunoassay can be performed according to the method of the present invention. In this method the fibrous matrix 22 is treated with a material that causes the surface to be positively charged, like water soluble polymeric materials with quaternary ammonium groups. Commercially available Celquat ™ L-200 (Polycationic Surfactant) (from National Starch and Chemical Company, Bridgewater, N.J.) or more preferably Merquat ™-100 (Polydimethyldiallylamonium chloride) (from Calgon, Pittsburgh, Pa.) can be used for this purpose. The sample is incubated in the shallow incubation well with a labeled antibody for the analyte, a capture phase is then added which is composed of the analyte molecule chemically bound to a an anionic polymer such as polyglutamic acid. After a second incubation the reaction mixture is transferred to the fibrous matrix using injected transfer solution.

Chemiluminescent moieties can be used as probes or labels in a specific binding assay. For example, chemiluminescent labels, such as acridinium sulfonamides, can directly react with an activator or activating reagent, such as alkaline peroxide, to generate a light signal. Alternatively, an enzyme label, such as alkaline phosphatase, can serve as a catalyst to generate light from a chemiluminescent substrate, such as a dioxetane aryl phosphate substrate. Acridinium sulfonamides labeling chemistry, as described in a co-pending U.S. patent application Ser. No. 371,763 entitled "Chemiluminescent Acridinium Salts", filed Jun. 23, 1989, incorporated herein by reference, may be employed according to the present invention for making a stable chemiluminescent tracer of high quantum yield. Alkaline phosphatase labeling techniques known in the art and use of dioxetane catalyzed chemiluminescence may be also used according to the present invention to generate a long-lived signal that can be integrated to yield high sensitivity assays.

The combination of these techniques are particularly useful to permit a simple, rapid, highly sensitive immunoassay method for determination of viral particles, macromolecular antigens and haptens. One such assay for Hepatitis B Surface antigen has sensitivities which exceed those of other methods. For example, one such type chemiluminescence immunoassay for Hepatitis B surface antigen (*Clin. Chem*, 27, 1378–1384 (1981)) involves two incubation periods, 1.5 hours each, and has a lower limit of detection of 2 ng/mL. A lower limit of detection of 1 ng/mL is achieved by increasing the incubation time to 16 hours. Using the detection device and method described according to the present invention, sub-nanogram quantities of Hepatitis B surface antigen may be detected within a total assay time of about one hour.

According to a preferred embodiment of this invention, a sandwich immunoassay is performed employing either a microparticle or a polyanionic acid, such as polyglutamic acid, which is attached to an antibody or to the analyte under determination, and added to a reaction vessel, either simultaneously or sequentially, with the analyte from the test sample and a chemiluminescent-labeled antibody. The reaction mixture is incubated for a period of time and under conditions which maximize the specific binding reaction. The reaction mixture is then transferred to the read well. Transfer of the reaction mixture into the read well of the two well device described above and shown in FIG. 1 can be achieved by a non-contact hydraulic or fluidic means such as described by U.S. Pat. No. 5,006,309 entitled "Device and Methods for performing a Solid-Phase Immunoassay, filed Apr. 22, 1988, incorporated herein by reference. Alternatively, transfer of the reaction mixture into the read well can be achieved by mechanical means such as a manual or automated pipettor.

The chemiluminescence signal from acridinium labeled assays is triggered and simultaneously detected on the fibrous matrix in the light-tight compartment formed from the disposable device and a detector head such as the detector head described in U.S. Pat. No. 5,089,424 and U.S. patent application Ser. No. 630,344

(filed Dec. 17, 1990 now abandoned), both incorporated herein by reference. The signal is integrated over a period of time longer than the sum of the rise and decay times of the chemiluminescence signal, but shorter than the residence time of the triggered reaction mixture in the fibrous matrix.

Alternatively, a sandwich immunoassay is performed employing a polyanionic acid such as polyglutamic acid which is attached to an antibody or to the analyte under determination, and added to a reaction vessel, either simultaneously or sequentially, with the analyte from the test sample and an enzyme-labeled antibody. Alkaline phosphatase or β-galactosidase-labeled antibody or antigen may be used. The reaction mixture is incubated for a period of time and under conditions which maximize the specific binding reaction. The reaction mixture is similarly transferred to a separation and detection chamber as described above. A long-lived chemiluminescent signal generating indicator may be added thereto to generate a chemiluminescent signal from the fibrous matrix in the separation and detection chamber before the device is mated with the detector head to form a light-tight compartment where the chemiluminescence signal is detected. The signal is integrated over a period of time longer than the sum of the rise and decay times of the chemiluminescence signal, but shorter than the residence time of the triggered reaction mixture in the fibrous matrix.

Similarly, competitive immunoassays using such chemiluminescent labeled antigen, antibody or other binding protein, or fragments thereof can also be prepared and used in the present invention. The device of the present invention may also be utilized with other assay methods, such as amplified heterogeneous chemiluminescent immunoassay methods described in co-pending U.S. patent application Ser. No. 611,235, filed Nov. 9, 1990, incorporated herein by reference, which utilize antigen coated microparticles, antigen-biotin conjugates and chemiluminescent compound labeled anti-biotin antibody to detect the presence or amount of anti-antigen antibody in a sample.

Preferably, according to the present invention, incubation and separation steps take place in two independent compartments. This limits the time during which the sample and conjugate are in contact with the fibrous matrix and the walls of the detection compartment. Thus the amount of sample and labeled conjugate that binds non-specifically to the fibrous matrix and wall of separation and detection compartment is substantially reduced as compared to incubation, wash and detection in the same well as described in U.S. Pat. No. 4,652,533, in *J. Immuno. Methods,* 67, 21–35 (1984), or *Clin. Chem.,* 32, 1682–1686 (1986), and accordingly, results in improved assay sensitivity.

Acridinium sulfonamide or ester labels are triggered by the addition of an alkaline peroxide solution to produce a short lived chemiluminescence signal. Because such chemiluminescence signals are short-lived, the activation of the chemiluminescent label is affected within a light-tight compartment, preferably created by mating the detector head with the disposable device. Long-lived dioxetane-type chemiluminescence is generated by adding an enzyme specific chemiluminescent substrate to the enzyme-labeled immune complex on the fibrous matrix. An example is the commercially available alkaline phosphatase substrate 3-(2'-spiroadamantane)-4-methoxy-4-(3''-phosphoroxy)phenyl-1,2-dioxetane disodium salt (AMPPD) from Tropex Inc., Bedford, Mass. Other examples are disclosed in U.S. Pat. Nos. 4,857,652; 4,931,223; 4,931,569; 4,962,192; 4,978,614; and 5,004,565. The enzyme substrate can be incubated before the disposable device engages the detector head and start of signal integration.

The hydrogen peroxide concentration in the alkaline peroxide solution used to trigger the chemiluminescent reaction on the fibrous matrix is kept within a range of about 0.1 to about 1.0 percent by volume in a sodium hydroxide solution having a concentration within the range of about 0.1 to about 0.25N. A preferred concentration is about 0.3% hydrogen peroxide solution in about 0.25N sodium hydroxide solution. Typically chemiluminescent reactions in solution are triggered with alkaline hydrogen peroxide containing approximately 0.03% by volume hydrogen peroxide in 0.1–0.25N sodium hydroxide solution. Higher concentrations of the trigger solution generate higher signal in a short period of time, possibly before triggered reaction mixture diffuses through the fibrous matrix.

IMPROVEMENTS

The inventors have discovered that the absorbent material (typically cellulose acetate, commercially available from American Filtrona Company, Richmond, Va.) of the read well chemiluminesced when the alkaline peroxide solution was added to the absorbent material. The observed chemiluminescence intensity varied between different manufacturing lots of the absorbent material and its contribution to the total signal could not be readily accounted for in the assay chemiluminescent signal. In addition, the inventors also observed chemiluminescence in neighboring wells of the device shown in FIG. 1, which was apparently a result of light leakage through the absorbent material from adjacent wells. Such background chemiluminescence reduces the sensitivity, accuracy and precision of an assay.

The inventors further discovered that this background chemiluminescence surprisingly could be substantially reduced by the use of an absorbent material which had light absorbing properties greater than that of a white absorbent material. "Light absorbing material" 21 (FIG. 4) means porous material pigmented or colored other than white having properties such that the quantum of measurable chemiluminescence generated in or capable of passing through the pigmented porous material is substantially less than the quantum of measurable chemiluminescence generated in or capable of passing through white or non-pigmented porous material composed of the same material. Cellulose acetate fiber material containing carbon black, preferably Transorb ® Reservoir, black (commercially available from American Filtrona Company, Richmond, Va., and prepared from Eastman Estron ® acetate tow, filtration grade, X-shaped fiber, No. 40, cross-section 5.0, Dernier/filament total 40,000) was effective in substantially reducing background chemiluminescence in the absorbent pad of the read well and is a preferred light absorbing material useful in the present invention. Black polycarbonate absorbent materials may be an alternative light absorbing material useful in the present invention. Polycarbonate absorbent materials can be rendered black with Irgalan black (Color Index, acid black 107) by soaking the material in a solution of Irgalan black in 2% acetic acid (2 g/L) for 24 hours, washing with water and drying at room temperature or at 82° C. for fifteen minutes. One skilled in the art can readily conceive of other materials having such light absorbing properties which can be used.

Alternatively, a layer of light absorbing material may be placed between the fibrous material and the absorbent pad, such that the reaction mixture may pass through the light absorbing layer into the absorbent pad but substantially reducing the quantum of chemiluminescent light produced in the absorbent layer which reaches the detector above the fibrous matrix. The black cellulose acetate fiber material may be used as the absorbent pad of the read well or may be used as a light barrier between the absorbent pad and the fibrous matrix of the read well. In the latter case, the required thickness or quantity of black cellulose acetate fiber used as a light barrier would be substantially less than the required thickness or quantity of black cellulose acetate fiber required for use as an absorbent pad; because the absorbent pad has the added function of absorbing liquid from the read well. Alternatively, the layer of light absorbing material may be a black mesh material (a fine synthetic fiber mesh), such as black colored nylon (polyamide) #PA 120/44 (commercially available from Saati Corporation, Industrial Fabrics Division, Stamford, Conn.) which has a mesh opening of 120 microns, a mesh count of 140 threads per inch, a thread diameter of 61 microns and a thickness of 110 microns.

Yet another alternative involves utilizing multiple layers of absorbent material in the present invention. Only the top absorbent layer adjacent to the fibrous matrix need have light absorbing properties greater than white absorbent material. The absorbent pad may be constructed in layers of white absorbent material, such as cellulose acetate, and black cellulose acetate so long as the top layer adjacent to the fibrous matrix is the black cellulose acetate layer.

The inventors further discovered an additional advantage to utilizing such light absorbing material in the present device. The light absorbing layer also reduces extraneous light from reaching the detector through the bottom or sides of the device. Thus the bottom and sides of the device need not be light-tight in order to form a light-tight seal between the device and the detector head.

Additionally, the inventors further discovered that the present device utilizing a binderless fibrous material surprisingly further improves the sensitivity of assays performed with the device. The inventors discovered that the use of binderless fibrous material resulted in reduced chemiluminescent signal in assays of samples containing none of the analyte of interest (negative samples) and increased chemiluminescent signal in assays of samples containing the analyte of interest (positive samples). Binderless fibrous material can be chosen from any of a variety of materials such as glass, cellulose, nylon or other natural or synthetic fibrous material well known to those skilled in the art wherein such materials are formed without the aid of binder. A suitable material is binderless glass fiber filter paper, which has a nominal thickness of about 0.055 inches. A preferable binderless fibrous material is #F315-03 unbound glass grade having a mean pore size by the bubble point method of about 4 microns with a particle retention size filtration range of about 3 to about 10 microns and a 98% capture efficiency for latex microparticles having a diameter within the range of about 1.2 to about 1.4 microns (commercially available from Whatman Paper Ltd., Specialty Products Division, Springfield Mill, Maidstone, Kent ME142LE, England). The thickness of such material is not critical, and is a matter of choice for one skilled in the art, largely based upon the properties of the sample being assayed, such as fluidity. In addition, as discussed in detail above, the pore size or spatial separation of the fibers must allow adequate void areas to assure the proper flow of reagents and sample through the fibrous matrix.

The present invention can be utilized in any device comprising a well, a fiber matrix layer and an absorbent layer below the fiber matrix, such as the devices disclosed in U.S. Pat. Nos. 5,149,622, 4,999,163 and 4,632,901. In addition, the present invention can also be utilized in any device comprising a well, a fiber matrix layer and a reservoir, where the interactive property of the matrix retains or retains and immobilizes a capture agent and the reaction mixture in the well is separated by the use of vacuum below the matrix or pressure above the matrix such that the reaction mixture not retained in the fibrous matrix passes into the reservoir. In such devices one skilled in the art can add a light absorbing layer below the fibrous matrix to substantially reduce chemiluminescent light generated in the reservoir from reaching a detector above the fibrous matrix. Further multilayer devices, such as the devices disclosed in U.S. Pat. Nos. 4,363,874 and 3,992,158, can also utilize the present invention to perform chemiluminescent assays on such devices. Typically, such devices comprise at least one reagent containing layer and a detection layer where the presence of the analyte of interest is,detected. One skilled in the art can readily incorporate a light absorbing layer between the reagent layer and the detection layer or utilize a light absorbing material containing the desired reagent in place of the reagent layer adjacent to the detection layer.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

Preparation Of A Reaction Tray

A disposable reaction tray was constructed according to the embodiments of this invention as described hereinabove from two injection molded parts. The disposable tray was 6.800 inches long, 3.125 inches wide, and 0.800 inches high. The top part incorporated a two by eight rectangular array of the shallow incubation wells. Associated with each incubation well was the funnel-like structure (read well) and the passage way between them described hereinabove. The capacity of the incubation well was 280 microliters and the capacity of the funnel was 480 microliters. The center to center spacing of the two adjacent incubation wells or two adjacent funnels was 1.4173 inches (36 mm). The pitch of the rows of consecutive wells was 0.800 inches. The funnel like structure had a cutting edge on the inside surface. The height of the surface feature for light sealing was 0.040 inches and its width was 0.040 inches. The vent hole was located 0.250 inches from the edge of the light baffle and was 0.060 inches in diameter. The top part was injection molded of black ABS. The bottom part was an injection molded piece of white ABS which mates with the top part and was sonically welded to it. The top and bottom parts had surface features to fix a slab of absorbant material in place. The top part of the disposable device was turned upside down and a sheet of fibrous glass was placed inside the disposable, covering the bottom part of the read wells. The fibrous material was pressed against the cutting edges of, the bottom of the funnel-like structures to cut individual filter matricies for each well. The over-all diameter of each matrix was 0.350 inches. The active area, facing the detector, was 0.210 inches in diameter. After the fiber matrix was press-cut, the rest of the sheet was removed. This method of cutting the fibrous matrix, removing the excess material, and having an individual fibrous matrix for each well was preferred as it prevents seepage of fluids between two adjacent wells and improved assay sensitivity. The absorbent material was placed in the top part of the disposable in contact with the glass fiber matricies. It was a rectangular slab 6.5 inches long, 3 inches wide and 0.265 thick. The material was bonded cellulose acetate, Transorb ® Reservior, white (commercially available from the American Filtrona Company, Richmond, Va., and prepared from cellulose acetate tow from Hoechst-Celanese). The absorbant pad was pressed against the glass fiber matricies by the bottom part. The surface features on the bottom part was in the form of a group of rings, each ring was concentric with one of the funnel-like structures and had a diameter of 0.665 inches with a rib 0.120 inches high. The preferred design ring pushed the pad of absorbant material against the glass fibrous matrix and assured intimate contact between the two layers. The two parts were assembled and welded using a Branson ultrasonic welder, Branson Ultrasonics, Danberry, Conn., with a horn optimized to fit the disposable device.

A transfer device similar to that described in the embodiments of this invention was constructed. Sample and reagents were incubated in the shallow incubation well. Transfer solution was injected from an group of three adjacent nozzles 0.5 mm nominal inside diameter made of Teflon ® tubing and connected to a machined polyacrylic manifold by minstac fittings from the Lee Company, Westbrook, Conn. The manifold was connected through a solenoid activated three way valve (Angar Scientific, Florham Park, N.J.) to a stepper motor controlled syringe pump. The nozzles were directed at an angle of 13° to the tangent to the shallow well surface at its point of intersection with reaction mixture surface. In this geometry the nozzles were at a 60° angle to the horizontal plane. Transfer solution was injected in the manifold at the rate of 1250 µL per second. The average linear injection speed was 2.1 m/second. The exit angle of fluid was 28°. Two aliquots 300 µL each of transfer solution were injected into the incubation well to affect transfer. A delay time of 10 seconds was allowed between the two injections to allow for the fluids to drain through the fibrous matrix. The capacity of the funnel was sufficient to prevent wash back. Transfer solutions preferably contained an amount of detergent such as 0.025–0.1% Tween ®20, 0.025–0.1% sodium lauryl sulfate or lithium lauryl sulfate to prevent beading of fluids in the incubation well and facilitate fluid transfer.

Three additional nozzles were installed in the transfer device and centered on the fibrous matrix. They were used either in groups or independently to wash the reaction mixture off the walls of the funnel into the matrix with a wash solution or to deliver conjugate solution to the matrix.

EXAMPLE 2

Reaction Transfer From Incubation To Read Wells

The method of transfer and the function of the transfer device was tested by determining the efficiency of transfer of labeled chemiluminescent microparticles from the incubation well to the read well of the disposable device of Example 1, using the following method:

Acridinium sulfonamide labeled antibody to Hepatitis B core antigen, at a concentration of about 5 µg/mL, was diluted in conjugate diluent, containing 50% fetal calf serum, 2% human plasma, 0.1% Tween ®-20, 0.1% ethylenediaminetetraacetic acid and 0.1% sodium azide in phosphate buffered saline, pH 6.8, to a final conjugate concentration of about 150 ng/mL. Carboxylated polystyrene microparticles coupled to antibody to Hepatitis B core antigen as an undercoat and then with recombinant Hepatitis B core antigen were pooled from lots prepared for clinical trials and contained 0.3% solids by weight. Microparticles were suspended in phosphate buffered saline, pH 7.2, containing 16% sucrose. A 0.1% solution of Tween ®-20 in phosphate buffered saline, pH 7.2, was used as a transfer solution.

Luminescent microparticles for the determination of transfer efficiency were prepared by mixing 50 mL of conjugate solution and 50 mL of microparticles suspension. The reaction mixture was incubated in a water bath at 40° C. for two hours. It was then left standing at room temperature for 24 hours to ensure complete binding of acridinium sulfonamide labeled antibodies to the antigen labeled microparticles.

100 µL of luminescent microparticles and 100 µL fetal calf serum were dispensed in each of the 16 shallow incubation wells of a disposable described in Example 1. The disposable reaction tray was placed on a linear track and moved to a position where it was located under the transfer device of the present invention. The mixture was transferred from the shallow incubation well to the read well using two 300 µL pulses of transfer solution. Two aliquots of 300 µL each of the transfer solution were injected at a linear speed of 2.1 m/second from three nozzles into the incubation well to transfer the serum and microparticles into the read well. The disposable tray was linearly moved to a subsequent position where the transferred microparticles on the matricies were triggered using 0.3% alkaline peroxide solution. Trigger solution was prepared by dissolving peroxide in 0.25M sodium hydroxide to yield an effective peroxide concentration of about 0.3%. The resulting chemiluminescence was measured using a detector head. Each side or row of well pairs (Side A and Side B, each side having 8 well pairs) of the disposable reaction tray was detected by an independent photomultiplier tube. The measured signal for each well was considered to correspond to the amount of the reaction mixture transferred from the incubation well to the read well. The mean and standard deviation for the eight wells on each side of the disposable were calculated.

A base line was determined by dispensing 100 µL of luminescent microparticles onto the fiber glass matrix in each of the 16 read wells of a disposable reaction tray of Example 1 and the microparticle solution was allowed to drain through. 100 µL of fetal calf serum and 100 µL of de-ionized water were dispensed in each of the shallow incubation wells of the same disposable. The disposable reaction tray was placed on a linear track and moved to a position where it was located under a transfer device of the present invention. Two aliquots 300 μL each of the transfer solution were injected at a linear speed of 2.1 m/second from three nozzles into the incubation well to transfer the serum and water mixture onto the fiber glass matrix with the microparticles using the same volume of fluids as before, and the disposable tray was moved on the same track by the same mechanism to the reader position under a detector head. The microparticles on the matrix were activated using alkaline peroxide solution and the resulting chemiluminescence signal was integrated for a period of six seconds. The mean and standard deviation of the signals generated in all eight wells of each side of each tray were calculated. The mean value of signal counts for the particles manually pipetted on the matrix corresponds to a 100% transfer.

The efficiency of transfer was calculated by dividing the magnitude of the mean signal generated from the transferred microparticles on each side by the signal representing 100% transfer on a corresponding side.

Precision of transfer of the reaction mixture from the incubation well to the read well was determined by repeating each of the two previously described transfer and base-line experiments on three disposable trays. The mean percent transfer and the % CV of the percent transfer were calculated for each side of the three trays. The experiments were repeated for six independent transfer devices mounted on six incubation tunnels. Each incubation tunnel was equipped with a read head and associated electronics controlled by an 310 development system (Intel corporation, Sunnyvale, Calif.). In all instances the transfer efficiency was higher than 95% and the % CV of transfer was well below 5%.

EXAMPLE 3

Microparticle-Capture Competitive Binding Assay for Hepatitis B Anticore Antibody.

Materials:

Acridinium sulfonamide labeled antibody to Hepatitis B core antigen (HBc), at a concentration of about 5 μg/mL, was diluted in conjugate diluent, containing 50% fetal calf serum, human plasma, 0.1% Tween®-20, 0.1% ethylenediaminetetraacetic acid and 0.1% sodium azide in phosphate buffered saline, pH 6.8, to a final conjugate concentration of about 150 ng/mL. Carboxylated polystyrene microparticles were coupled to anti-Hepatitis B core antigen antibody (HBc antibody) and then the HBc antibody particles were incubated with recombinant Hepatitis B core antigen and washed. The HBc coated microparticles were suspended (about 0.3% solids by weight) in phosphate buffered saline, pH 7.2, containing 16% sucrose. A 0.1% solution of Tween® 20 in phosphate buffered saline, pH 7.2, was used as a transfer solution. Trigger solution was prepared by dissolving peroxide in 0.25M sodium hydroxide to yield effective peroxide concentration of about 0.3%.

HBc antibody negative controls and HBc antibody positive controls from a commercial enzyme immunoassay kit that has 50–60% inhibition as measured by a commercial enzyme immunoassay procedure (Corezyme, Abbott Laboratories, North Chicago, Ill.) were used in the following two procedures:

Procedure A: Automated One Step Assay:

100 μL of control or sample were dispensed into the shallow incubation wells of the disposable device of Example 1. Then 50 μL of acridinium labeled HBc antibodies and 50 μL of antigen coated latex particles were dispensed into the incubation wells. The reaction mixture was incubated for 40 minutes in a heated tunnel at 40° C. with the disposable device moving into the tunnel by a stepper timing belt at steps of 0.80 inches per second per step. Mean time between each step, when the device is stationary, was about 72 seconds.

The reaction mixture was transferred and then washed from the shallow incubation well onto the fibrous matrix of the read well. Transfer was accomplished by injecting two pulses of 300 μL each of the transfer solution into the incubation well from three nozzles in the transfer device. Each nozzle has a nominal diameter of 0.5 mm and the fluid was injected at an average linear speed of 2.1 m/second. A delay time of about 12 seconds was allowed between the two pulses to assure drainage of the transferred solution through the matrix.

The transferred microparticles, retained on the matrix in the read well, were subsequently washed with three aliquots, 100 μL each, of wash solution. The disposable was moved on the timing belt to allow subsequent well pairs to be located under the transfer device and to transfer the reaction mixture and wash the microparticles retained and entrapped on the fibrous matrix. The disposable device 10 was moved at the same rate to a read position where a chemiluminescence detector head (described in U.S. Pat. No. 5,089,424 and copending U.S. patent application Ser. No. 630,344, filed Dec. 17, 1990, both incorporated herein by reference) was lowered to mate with the walls surrounding the first two wells on the disposable to create a light-tight seal. The chemiluminescent labels on the microparticles on the fibrous matrix were triggered using the trigger solution. The measured signal for each well was considered to correspond to the amount of acridinium labeled conjugate attached to the microparticles. The end point was determined by calculating the percent inhibition of signal wherein % Inhibition = 100 (mean of Negative Control—Mean of Sample)/(Mean of Negative Control—Mean of Positive Control). A % inhibition of 50% and higher was taken as positive and a % inhibition less than 50% was assigned as negative.

The results are summarized in Table 1. Reproducibility of the percent inhibition figures indicate the validity of the fluid transfer method. Agreement with the standard enzyme immunoassay method shows that a heterogeneous immunoassay can be performed using the method and device of the present invention.

TABLE 1

| | One-Step Microparticle Capture Competitive Binding Hepatitis B Anticore Antibody Assay | | | | | | | |
|---|---|---|---|---|---|---|---|---|
| | Side A | | | | Side B | | | |
| Sample | Mean Counts | SD | % I | SD | Mean Counts | SD | % I | SD |
| Neg. Control (n = 71) | 37833 | 1028 | −1.5 | 3.00 | 35039 (n = 69) | 772 | −0.26 | 2.40 |
| Pos. | 2657 | 122 | 100.8 | 0.35 | 2174 | 109 | 100.7 | 0.34 |

TABLE 1-continued

One-Step Microparticle Capture Competitive Binding
Hepatitis B Anticore Antibody Assay

| Sample | Side A | | | | Side B | | | |
|---|---|---|---|---|---|---|---|---|
| | Mean Counts | SD | % I | SD | Mean Counts | SD | % I | SD |
| Control (n = 7) | | | | | | | | |
| Panel (n = 7) | 19106 | 884 | 52.8 | 2.58 | 17126 | 462 | 54.7 | 1.41 |

Procedure B: Automated Two Step Assay:

100 μL of control or sample were pipetted into the shallow incubation wells of the disposable device of Example 1. Then 50 μL of a solution of 50 mM cysteine, 10 mM EDTA and 0.01% gentamicin, and 50 μL of the antigen coated latex microparticles (see Materials above) were dispensed into each incubation well. The reaction mixture was incubated for 20 minutes in a heated tunnel at 40° C. with the disposable device moving into the tunnel using the same mechanism described for the one step procedure. The reaction mixture was transferred from the shallow incubation well onto the fibrous matrix of the read well as described in the One Step Assay of this Example 3. A 12 second delay was allowed for the transfer solution to drain down into the absorbant pad. The disposable was moved on the timing belt to allow subsequent well pairs to be located under the transfer device and to affect transfer of the reaction mixture. 50 μL of the solution of acridinium labeled HBc antibodies were dispensed on each fibrous matrix of the read wells from one of the nozzles located in the transfer device and directed on the center of the read well. The disposable device was incubated for 20 more minutes in the tunnel using the same moving timing belt as it is moved to a washing position.

The transferred microparticles, retained on the matrix in the read well, and the excess acridinium labeled antibodies were subsequently washed with three 100 μL aliquots, of wash solution. The disposable device was moved at the same rate to a read position where the chemiluminescent label on the microparticles on the fibrous matrix were triggered using the trigger solution and the chemiluminescence signal was integrated for six seconds. The measured signal for each well was considered to correspond to the amount of acridinium labeled conjugate attached to the microparticles.

The results are summarized in Table 2. A percent inhibition of 50% and higher was taken as positive and a percent inhibition less than 50% was assigned as negative.

TABLE 2

Two-Step Microparticle Capture Competitive Binding
Hepatitis B Anticore Antibody Assay

| Sample | Side A | | | | Side B | | | |
|---|---|---|---|---|---|---|---|---|
| | Mean Counts | SD | % I | SD | Mean Counts | SD | % I | SD |
| Neg. Control (n = 70) | 31610 | 1066 | 0.4 | 3.8 | 26839 | 583 | −1.3 | 2.5 |
| Pos. Control (n = 7) | 3399 | 391 | 101.7 | 1.4 | 3260 | 474 | 100.3 | 2.0 |
| Panel (n = 7) | 15452 | 988 | 58.4 | 3.5 | 14102 | 355 | 53.6 | 1.5 |

The cut-off value (the value below which a sample is considered negative) was established by assaying 200 negative samples that were confirmed negative for HBc antibody using an enzyme linked immunosorbent assay procedure (Corezyme, Abbott Laboratories, North Chicago, Ill.).

EXAMPLE 4

Ion-Capture Based Competitive Binding Hapten Chemiluminescence Immunoassay

This example shows the use of the device and method of this invention in a competitive binding assay for the abused drug phencyclidine (PCP) in urine employing ion capture immunoassay procedures described above. The formation of the immune complex in the shallow incubation well of the disposable device of Example 1 involves the use of an anionic polymer as part of the capture agent. The reaction mixture is transferred to the read well of said device and the immunochemical reaction product is immobilized by ionic forces on the fibrous matrix of said device that has been previously treated with a solution of a cationic polymer.

Anti-phencyclidine antibodies were labeled with acridinium sulfonamide using EDAC coupling procedures. Pre-wet and transfer solutions were IMx® buffer (Abbott Laboratories, North Chicago, Ill.) containing 25 mM TRIS, 0.3M sodium chloride, 0.1% sodium azide, pH 7.2. The cationic polymer was a 0.5% aqueous solution of Celquat TM L-200 (National Starch and Chemical Company; Bridgewater, N.J.) in 10 mM sodium chloride.

The capture agent, phencyclidine-polyglutamic acid (PCP-PGA), was prepared according to the following steps:

1 gm of polyglutamic acid sodium salt (Sigma Chemical Company, St. Louis, Mo.) was added to 7 gms of AG50W-X8 ion exchange resin (Bio-Rad, Richmond, Calif.) in 20 mL water and stirred overnight. The liquor was separated and lyophilized to yield polyglutamic acid free acid (PGAFA).

Phencyclidine-4-chloroformate was prepared by reacting 1.4 mg 4-hydroxyphenylcyclidine in 0.5 mL tetrahydrofuran with 0.5 mL of 10% solution of phosgene in benzene (130 mole excess). The reaction was allowed to proceed for 2.5 hours at room temperature. Solvent was evaporated under a stream of nitrogen to yield a residue of phenylcyclidine-4-chloroformate. The residue was dissolved in 0.5 mL tetrahydrofuran and 1.7 mg of free acid polyglutamic acid (molecular weight 40,000) in 0.5 mL 1-methyl-2-pyrrolidine was added. The reaction was stirred overnight at room temperature and then the reaction mixture was evaporated to dryness. The dried mixture was dissolved in 1.5 mL phosphate buffer, pH 7.0 and dialyzed against 0.1M sodium phosphate at pH 7.0 in a 30,000 molecular weight cut-off dialysis bag. The precipitate was filtered and dissolved in phosphate buffer. The cloudy aqueous filtrate was extracted with methylene chloride until the aqueous layer was clear. The aqueous layer was diluted in a buffer containing 1% fish gelatin, 25 mM TRIS, 100 mM sodium chloride, 1 mM magnesium chloride, 0.1 mM zinc chloride and 0.1% sodium azide at pH 7.2 to yield 5 µg/L PCP-PGA capture reagent.

Trigger solution was prepared by dissolving peroxide in 0.25M sodium hydroxide to yield effective peroxide concentration of about 0.3%.

Phencyclidine calibrators (TDx TM PCP FPIA Assay Kit, commercially available from Abbott Laboratories, North Chicago, Ill.) containing 500, 250, 120, 60, 25, and 0 ng/mL phencyclidine in human urine were assayed by the following procedure:

a) 50 µL of pre-wet solution followed by 50 µL Celquat TM solution were dispensed on the fibrous glass matrix of disposable reaction tray of the present invention.

b) 50 µL of control or sample were dispensed into the shallow incubation wells of the disposable device of Example 1. 50 µL of acridinium labeled anti-PCP antibodies were dispensed into each incubation well. The mixture was incubated for 9.8 minutes in a heated tunnel at 32° C. with the disposable device moving into the tunnel by a timing belt in steps at the rate of 0.8 inches per minute. The mean time between steps was 36 seconds when the device remained stationary. After the 9.8 minute incubation, 50 µL a solution containing PCP-PGA capture reagent was dispensed into the incubation well. The reaction mixture is further incubated for 9.8 minutes. The quaternary ammonium-polymer treated fibrous matrix was rinsed with 100 µL of IMx ® buffer before the reaction mixture was transferred.

c) The reaction mixture was transferred from the shallow incubation well onto the pretreated fibrous matrix in the read well. Transfer was affected by injecting a single pulse of 350 µL of IMx ® buffer into the well at a speed of 1250 µL per second from the three nozzles in the transfer device. The disposable was moved on the timing belt to allow subsequent well pairs to be located under the transfer device and to affect transfer of the reaction mixture. The disposable device was then moved to a read position, where a chemiluminescence detector head (described in U.S. Pat. No. 5,089,424 and co-pending U.S. patent application Ser. No. 630,344, filed Dec. 17, 1990, both incorporated herein by reference) was lowered to mate with the surface feature on the first two wells on the disposable to create a light-tight seal. The retained and immobilized immune complex on the matrix was triggered using the trigger solution and the signal was integrated for eight seconds. The measured signal for each well was considered to correspond to the amount of acridinium labeled conjugate attached to the fibrous matrix surface.

The measured concentration of PCP below which a sample is considered negative is at 25 ng/mL. The results, summarized in Table 3, show that all controls containing 25 ng/mL PCP or higher were well differentiated from the negative control.

Example 5

Microparticle-Based Sandwich CLIA For Hepatitis B Surface Antigen.

AD subtype and AY subtype Hepatitis B Surface antigen (HBsAg) sensitivity panels (AD subtype or AY subtype HBsAg purified from heat-inactivated HBsAg positive human serum spiked into HBsAg negative recalcified human plasma to predetermined concentrations), positive and negative controls for HBsAg (commercially available from Abbott Laboratories, North Chicago, Ill.) were assayed for HBsAg using the following procedure. An acridinium sulfonamide labeled goat anti-HBsAg polyclonal antibody conjugate was prepared and diluted to 0.17 µg/mL in conjugate diluent. Conjugate diluent was prepared by mixing 0.1M monosodium phosphate, 0.1M disodium phosphate, 0.1% sodium azide, 53% calf serum and 10% normal human serum. The conjugate diluent was filtered through 0.45 µm Nalgene disposable sterile filter (Nalge company, Division of Sybron Corporation, Rochester, N.Y.) and then the diluent pH was adjusted to a final pH of 6.3. Finally, the diluent was filtered through a 0.2 µm Nalgene Filter.

Trigger solution was prepared by dissolving peroxide in 0.25M sodium hydroxide to yield effective peroxide concentration of about 0.3%.

Carboxylated polystyrene microparticles (0.21 µm) were coupled to mouse IgM anti-HBsAg monoclonal antibodies using EDAC and a suspension of the microparticles was prepared with a total solids content of 0.24% (w/w).

A wash solution was prepared containing 0.1M borate, 0.02% lithium dodecyl sulfate, 0.9% sodium chloride and 0.1% sodium azide.

200 µL of control or sample were dispensed into the shallow incubation wells of a disposable tray described in Example 1. 30 µL of the microparticle solution were dispensed into the incubation wells. The reaction mixture was incubated for 20 minutes in a heated tunnel at 40° C. with the disposable device moving into the tunnel by a stepper timing belt at step increments of 0.8 inches per second per step. Mean time between each step, when the device is stationary, was about 72 seconds.

The reaction mixture was transferred from the shallow incubation well onto the fibrous matrix of read well using the method of Example 3 After the transfer solution drained down into the absorbant pad, 30 µL conjugate solution were dispensed onto each fibrous matrix. The disposable tray was incubated for 30 additional minutes in the tunnel using the same stepper timing belt and is moved to a washing position. The transferred microparticles that are retained on the glass fiber matrix and the added acridinium labeled antibodies were subse-

TABLE 3

Ion-Capture Competitive Binding Assay For Phencyclidine (PCP) in Urine

| PCP [ng/mL] | Side A | | Side B | |
|---|---|---|---|---|
| | Signal | % Bound | Signal | % Bound |
| 0 | 199886 | 0.00 | 181430 | 0.00 |
| 25 | 33752 | 83.00 | 27753 | 85.50 |
| 60 | 12412 | 94.60 | 12140 | 94.19 |
| 120 | 6818 | 97.44 | 6106 | 97.54 |
| 250 | 3223 | 99.28 | 2907 | 99.32 |
| 500 | 1803 | 100.00 | 1690 | 100.00 | quently washed with three aliquots, 100 μL each, of wash solution containing 0.1% sodium dodecyl sulfate, from a wash nozzle. The disposable tray is moved by the belt to a read position where a chemiluminescence detector head (described in U.S. Pat. No. 5,089,424 and co-pending U.S. patent application Ser. No. 630,344, filed Dec. 17, 1990, both

TABLE 4

Microparticle Capture Chemiluminescence Immunoassay for Hepatitis B Surface Antigen: Sensitivity Panel Data

| Sample | Concentration (ng/mL) | Counts/6 sec. | % CV |
|---|---|---|---|
| ADA | 1.90 | 19270 | 5.8 |
| ADB | 1.48 | 15659 | 6.2 |
| ADC | 0.92 | 10756 | 7.1 |
| ADD | 0.74 | 8945 | 4.9 |
| ADE | 0.51 | 6717 | 5.2 |
| ADF | 0.41 | 5751 | 5.3 |
| ADG | 0.31 | 4547 | 2.1 |
| ADH | 0.10 | 2840 | 4.2 |
| AYA | 2.05 | 23751 | 4.5 |
| AYB | 1.11 | 14242 | 3.7 |
| AYC | 0.83 | 11216 | 4.9 |
| AYD | 0.67 | 8455 | 2.2 |
| AYE | 0.53 | 7132 | 4.7 |
| AYF | 0.44 | 6295 | 4.8 |
| AYG | 0.30 | 4926 | 4.9 |
| AYH | 0.14 | 2911 | 4.0 |
| Neg. Control | | 1247 | 8.3 |
| Pos. Control | | 11521 | 6.1 | incorporated herein by reference) was lowered to mate with the surface features of the disposable to create a light-tight seal. The transferred and washed microparticles were triggered with the trigger solution. The measured signal for each well was considered to correspond to the amount of acridinium labeled conjugate attached to the microparticles and hence directly related to the concentration of the HBsAg in the sample. The results are summarized in Table 4.

The standard deviation for twelve replicates of the negative control is 104. The cut off value (the value below which a sample is considered negative) of the assay was determined to be 2287 counts by adding 10 standard deviations to the mean of the negative control. Thus concentrations of Hepatitis B Surface Antigen as low as 0.10 ng/mL of the AD subtype and 0.14 ng/mL of the AY subtype can be quantified using this microparticle capture chemiluminescence immunoassay. Using the same criterion to the data published in Table 4 of *Clin. Chem.* 27:1378–1384 (1981), yields a lowest limit of quantitation of 5 ng/mL. Thus a limit of quantitation of Hepatitis B surface antigen one order of magnitude lower than reported in the art can be achieved.

Example 6

Background Of Absorbant Pads

The device of Example 1 was prepared utilizing white cellulose acetate absorbent material, Transorb ® Reservoir, white (lot # P051410 and lot #1020192) or cellulose acetate absorbent material containing carbon black, Transorb ® Reservoir, black (each commercially available from American Filtrona Company, Richmond, Va.), but without the fiber matrix. Trigger solution was prepared by dissolving peroxide in 0.25M sodium hydroxide to yield effective peroxide concentration of about 0.3%. 400 μL of trigger solution was dispensed into each of the read wells of one tray and any resulting chemiluminescence from the read wells of the tray

TABLE 5

Chemiluminescence Of Absorbent Pads

| | Black Cellulose | | White Cellulose lot # P051410 | | White Cellulose lot # I020192 | |
|---|---|---|---|---|---|---|
| | Side A | Side B | Side A | Side B | Side A | Side B |
| mean* (n = 8) | 83 | 61 | 505 | 503 | 2828 | 1799 |
| SD** | 12 | 7 | 55 | 96 | 299 | 243 |
| % CV | 14 | 12 | 11 | 19 | 11 | 14 |

*mean = the mean chemiluminescent signal intensity (counts/6 sec.).
**SD = standard deviation.

was detected using a pair of the detectors described above. One detector read the eight wells on the left side of the tray (Side A) and one detector read the eight wells on the right side of the tray (Side B). The results summarized in Table 5 demonstrate that the black cellulose acetate absorbent material had substantially reduced the chemiluminescence from the absorbent material.

Example 7

Background Of Absorbant Pads In HBsAg Assay

The device of Example 1 was prepared utilizing white cellulose acetate absorbent material, Transorb ® Reservoir, white, or cellulose acetate absorbent material containing carbon black, Transorb ® Reservoir, black (each commercially available from American Filtrona. Company, Richmond, Va.). Heat-inactivated HBsAg negative human recalcified plasma was spiked with HBsAg purified from heat-inactivated HBsAg positive human serum to a final concentration of 0 ng/mL (negative control), 0.5 ng/mL (low positive control) and greater than 5 ng/mL (high positive control) of HBsAg. The controls were assayed for HBsAg according to the procedure

TABLE 6

HBsAg Assay Using White And Black Absorbent Pads

| | Black Cellulose | | | White Cellulose | | |
|---|---|---|---|---|---|---|
| | mean* | SD** | % CV | mean* | SD** | % CV |
| | Side A | | | Side A | | |
| Neg. (n = 8) | 135 | 12 | 8.6 | 675 | 36 | 5.3 |
| Low (n = 12) | 1365 | 30 | 2.2 | 1980 | 47 | 2.4 |
| High (n = 12) | 25838 | 817 | 3.2 | 28100 | 605 | 2.2 |
| | Side B | | | Side B | | |
| Neg. (n = 8) | 136 | 11 | 8.4 | 789 | 29 | 3.7 |
| Low (n = 12) | 1328 | 39 | 2.9 | 2035 | 68 | 3.3 |
| High (n = 12) | 25938 | 454 | 1.8 | 27858 | 599 | 2.2 |

*mean = the mean chemiluminescent signal intensity (counts/6 sec.).
**SD = standard deviation.

described in Example 5 using the trays containing white and black cellulose acetate absorbent material. Four of each tray type were used and the resulting chemiluminescent signal generated in the assays on each tray was detected using a pair of the detectors described above. One detector read the eight wells on the left side of the tray (Side A) and one detector read the eight wells on the right side of the tray (Side B). The results summarized in Table 6 demonstrate that the black cellulose acetate absorbent material had substantially improved the HBsAg assay by reducing background chemiluminescence.

Example 8

HBsAg Assay Sensitivity Panel Data With White And Black Absorbent Pads

The device of Example 1 was prepared utilizing white cellulose acetate absorbent material, Transorb ® Reservoir, white, or cellulose acetate absorbent material containing carbon black, Transorb ® Reservoir, black (each commercially available from American Filtrona Company, Richmond, Va.). AD subtype and AY subtype Hepatitis B Surface antigen (HBsAg) sensitivity panels (AD subtype or AY subtype HBsAg purified from heat-inactivated HBsAg positive human serum spiked

TABLE 7

HBsAg Assay Sensitivity Panel Data

| Sample | Conc. (ng/mL) | Black Cellulose mean* | S/N | White Cellulose mean* | S/N |
|---|---|---|---|---|---|
| AY1 | 2.30 | 7466 | 51.8 | 8623 | 11.9 |
| AY2 | 1.59 | 5251 | 36.5 | 6088 | 8.4 |
| AY3 | 0.92 | 2963 | 20.6 | 3628 | 5.0 |
| AY4 | 0.84 | 2541 | 17.6 | 3372 | 4.7 |
| AY5 | 0.62 | 1854 | 12.9 | 2441 | 3.4 |
| AY6 | 0.45 | 1373 | 9.5 | 2074 | 2.9 |
| AY7 | 0.29 | 1027 | 7.1 | 1688 | 2.3 |
| AY8 | 0.17 | 605 | 4.2 | 1306 | 1.8 |
| AD1 | 2.18 | 4564 | 31.7 | 5489 | 7.6 |
| AD2 | 1.51 | 3263 | 22.7 | 4078 | 5.6 |
| AD3 | 0.92 | 1863 | 12.9 | 2737 | 3.8 |
| AD4 | 0.77 | 1598 | 11.1 | 2510 | 3.5 |
| AD5 | 0.49 | 1201 | 8.3 | 2131 | 2.9 |
| AD6 | 0.37 | 936 | 6.5 | 1710 | 2.4 |
| AD7 | 0.23 | 768 | 5.3 | 1464 | 2.0 |
| AD8 | 0.10 | 468 | 3.2 | 1217 | 1.7 |

*mean = the mean chemiluminescent signal intensity (counts/6 sec.).

into HBsAg negative recalcified human plasma to predetermined concentrations listed in Table 7) were assayed for HBsAg using the procedure of Example 5 and the trays containing white and black cellulose acetate absorbent material. The results summarized in Table 7 demonstrate that the black cellulose acetate absorbent material had substantially improved the HBsAg assay sensitivity as shown by the improved signal-to-noise ratio (S/N).

Example 9

Microparticle-Based CLIA For Anti-HIV Antibody Utilizing Black And White Absorbent Pads A. Preparation of Acridinium-Labeled Anti-Biotin One (1) mg of 10-methyl-9-(N-tosyl-N-(2-carboxyethyl))acridine carboxamide was dissolved in 100 µL of DMF, and then treated with 50 µL of a 5.75 mg/mL DMF solution of N-hydroxy-succinimide and 50 µL of 9.75 mg/mL DMF solution of 1-ethyl-3-(3-dimethylaminopropyl)carbodiimide. The solution then was allowed to stir at ambient room temperature overnight. The activated acridinium derivative then was coupled to anti-biotin as follows. The antibody was dialyzed against 0.1M phosphate (pH 8.0), containing 0.15M NaCl, and the protein then was adjusted to a concentration of 1 mg/mL in the same buffer. The activated acridinium derivative at a 5 to 10 molar excess then was added to the antibody solution at room temperature. After ten (10) minutes, the reaction mixture was centrifuged (12,000 rpm for two (2) minutes) to remove aggregates, and the supernatant solution then was applied to a TSK-250 gel filtration column, which previously had been equilibrated with 0.01M sodium phosphate, pH 6.3, containing 0.15M NaCl. One mL fractions were collected, and the absorbance monitored at 280 nm and 369 nm. Fractions containing the IgG peak were pooled, and the extent of acridinium incorporation was calculated as follows: protein concentration was determined using absorbance at 280 nm corrected for the contribution made by acridinium at this wavelength (corrected absorbance = $A^{280} - [A^{369} \times 0.247]$). Moles of acridinium and IgG were calculated using a molar extinction coefficient of 14,650 and 220,000 $M^{-1}$ $CM^{-1}$, respectfully.

B. Preparation of HIV Antigen Coated Microparticles

HIV antigen (10 mg) in 34.28 mL of 0.5M borate buffer (pH 8.5) is mixed with 10 mL of a 0.5% solids suspension of polystyrene latex particles, and then 55.72 mL of deionized water was added. The suspension was then allowed to stir overnight at room temperature. The solids were then isolated by centrifugation (17,000 rpm for 30 minutes) and then purified by three cycles of resuspension-centrifugation in 0.1M phosphate buffer (pH 7.0) containing 0.1% Tween ®. The coated particles were then resuspended, allowed to stir gently at 56° C. for one (1) day, and then stored at room temperature prior to use.

C. Preparation of Biotinylated HIV Antigen

HIV antigen (1.9 mg) in 2.278 mL of 0.1M borate buffer (pH 8.5), containing 250 mM NaCl and 0.1% sodium azide, was treated with 0.125 mL of 10% Triton ® for 30 minutes. Then, 97 µL of 5 mg/mL of biotinamidocaproate N-hydroxysuccinamide ester dissolved in DMF, was added. The reaction mixture was allowed to stir at room temperature for about two (2) hours. The mixture was dialyzed extensively against 0.1M borate buffer (pH 8.5) containing 250 mM NaCl, 0.1% SDS, and 0.1% sodium azide.

D. Assay for HIV

Fifty (50) µL of an approximately 0.2% solid suspension of HIV antigen coated microparticles in a pH 7.0 solution of 11% sucrose (w/w %), 0.01M EDTA, 0.1% CHAPS ®, 0.1M phosphate buffer and 0.1% sodium azide was added to 100 µL of sample in an incubation well of a disposable tray described in Example 1. The suspension was then allowed to incubate for about 20 minutes at 40° C. before being transferred to the capture membrane by two successive 300 µL washes of pH 8.5, 0.1M borate buffer, 0.15M NaCl, and 0.01% lithium dodecylsulfate (LDS) containing 0.1% sodium azide.

The washed suspension then was allowed to incubate for about ten (10) minutes at 40° C. before it was treated with 30 µL of 750 ng/mL solution of biotinylated HIV antigen in 0.1M borate buffer (pH 8.5), 1%, E. coli lysate, 500 µg/mL CKS, 12.5% calf serum, and 1.0% Cholic Acid containing 0.1% sodium azide. The capture membrane then was allowed to incubate for 20 minutes before it was washed with three (3) 100 µL portions of a pH 8.5 wash solution which comprised 0.1M borate, 0.15M NaCl, and 0.03% LDS containing 0.1% sodium azide. The washed capture membrane then was treated with 30 µL Of a 167 ng/mL solution of the anti-biotin antibody coupled to acridinium sulfonamide in 0.01M phosphate (pH 6.3), 0.15M NaCl, 5% BSA, and 1.0% Triton ® containing 0.1% sodium azide. After a further ten (10) minute incubation at 40° C., the capture membrane was washed with five (5) 100 µL portions of a pH 8.5 solution of 0.1M borate, 0.15M NaCl and 0.01% LDS, containing 0.1% sodium azide. The washed capture membrane then was incubated for ten (10) minutes at 40° C. prior to being treated with an alkaline peroxide solution (0.25N NaOH containing 0.3% peroxide). The chemiluminescence was read for six (6) seconds and the presence or absence of anti-HIV was determined, as described in more detail in Example 9E hereinafter.

E. Black Verses White Absorbent Pads

The device of Example 1 was prepared utilizing white cellulose acetate absorbent material, Transorb® Reservoir, white, or cellulose acetate absorbent material containing carbon black, Transorb® Reservoir, black (each commercially available from American Filtrona Company, Richmond, Va.). Anti-HIV antibody negative recalcified human plasma (negative control) and heat-inactivated anti-HIV antibody positive recalcified human plasma spiked into negative control (positive control) were assayed for anti-HIV antibody according to the general procedure described in Example 9D using the trays containing white and black cellulose acetate absorbent material. The general method described in Example 9D was modified only in the volume (30 μL or 50 μL) of the biotinylated HIV antigen ("probe") solution and/or the antibiotin antibody coupled to acridinium sulfonamide ("conjugate") solution used in the assay. Each control was assayed in triplicate on each row (Side A or B) of each tray type using each combination of probe and conjugate solutions volumes as listed in Table 8. The resulting chemiluminescent signal generated in the assays on each tray was detected using a pair of the detectors described above. One detector read the wells on the left side of the tray (Side A) and one detector read the eight wells on the right side of the tray (Side B). The results summarized in Table 8 demonstrate that the black cellulose acetate absorbent material had substantially improved sensitivity of the anti-HIV antibody assay by reducing background chemiluminescence and increasing the

TABLE 8

Anti-HIV Antibody Assay With Varied Volumes Of Probe And Conjugate

| Sample | Volume | | White Cellulose | | Black Cellulose | |
|---|---|---|---|---|---|---|
| | Probe (μL) | Conjug. (μL) | mean (n = 6) | S/N | mean (n = 6) | S/N |
| neg. | 30 | 30 | 3553 | | 2038 | |
| pos. | 30 | 30 | 52571 | 14.8 | 47355 | 23.2 |
| neg. | 50 | 30 | 5148 | | 2469 | |
| pos. | 50 | 30 | 54740 | 10.6 | 49355 | 20.0 |
| neg. | 30 | 50 | 6539 | | 2036 | |
| pos. | 30 | 50 | 59001 | 9.0 | 51233 | 25.2 |
| neg. | 50 | 50 | 10230 | | 2461 | |
| pos. | 50 | 50 | 62451 | 6.1 | 47826 | 19.4 | signal-to-noise ratio (S/N). In addition, the chemiluminescent background in the assay performed on the tray with white cellulose acetate absorbent increased with higher volumes of probe and conjugate, but the chemiluminescent background in the assay performed on the tray with black cellulose acetate absorbent was not substantially affected at all.

Example 10

Matrix With And Without Binder In HBsAg Assay

The device of Example 1 was prepared utilizing cellulose acetate absorbent material containing carbon black, Transorb® Reservoir, black (commercially available from American Filtrona Company, Richmond, Va.) and either a fiber matrix of glass fiber containing binder (commercially available from Hollingsworth and Vose Co., West Groton, Mass.) or fiber matrix of glass fiber not containing binder (binderless) #F315-03 (commercially available from Whatman Paper Ltd., Specialty Products Division, Springfield Mill, Maidstone, Kent ME142LE, England). Heat-inactivated HBsAg negative human recalcified plasma was spiked with HBsAg purified from heat-inactivated HBsAg positive human serum to a final concentration of 0 ng/mL (negative control), 0.5 ng/mL (low positive control) and greater than 5 ng/mL (high positive control) of HBsAg. The controls were assayed for HBsAg according to the procedure described in Example 5 using the trays containing black cellulose acetate absorbent material and either glass fiber matrix with binder or glass fiber matrix without binder. The resulting chemiluminescent signal generated in the assays on each tray was detected using a pair of the detectors described above. One detector read the eight wells on the left side of the tray (Side A) and one detector read the eight wells on the right side of the tray (Side B). The results summarized in Table 9 demonstrate that the binderless glass fiber matrix had substantially improved the HBsAg assay by reducing background chemiluminescence.

TABLE 9

HBsAg Assay Using Matrix With And Without Binder

| | Matrix With Binder | | | Matrix Without Binder | | |
|---|---|---|---|---|---|---|
| | mean* | SD** | % CV | mean* | SD** | % CV |
| | Side A | | | Side A | | |
| Neg. | 138 | 14 | 10.0 | 78 | 13 | 17.1 |
| Low | 1788 | 68 | 3.8 | 1726 | 57 | 3.3 |
| High (n = 22) | 24892 | 731 | 2.9 | 25207 | 646 | 2.6 |
| | Side B | | | Side B | | |
| Neg. (n = 20) | 143 | 20.1 | 14.1 | 75 | 8 | 10.0 |
| Low (n = 22) | 1757 | 47.5 | 2.7 | 1685 | 56 | 3.3 |
| High (n = 22) | 24933 | 623 | 2.5 | 25202 | 519 | 2.1 |

*mean = the mean chemiluminescent signal intensity (counts/6 sec.).
**SD = standard deviation.

Example 11

Matrix With And Without Binder In Two-Step Microparticle Competitive Binding HBc Antibody Assay The device of Example 1 was prepared utilizing cellulose acetate absorbent material containing carbon black, Transorb® Reservoir, black (commercially available from American Filtrona Company, Richmond, Va.) and either a fiber matrix of glass fiber containing binder #AGC4111 (commercially available from Hollingsworth and Vose Co., West Groton, Mass.) or fiber matrix of glass fiber not containing binder (binderless) #F315-03 (commercially available from Whatman Paper Ltd., Specialty Products Division, Springfield Mill, Maidstone, Kent ME142LE, England). HBc antibody negative controls and HBc antibody positive controls from a commercial enzyme immunoassay kit that has 50–60% inhibition as measured by a commercial enzyme immunoassay procedure (Corezyme, Abbott Laboratories, North Chicago, Ill.) were assayed for anti-HBc antibody according to the Two Step Competitive Assay Procedure described in Example 3B using the trays containing black cellulose acetate absorbent material and either glass fiber matrix with binder or glass fiber matrix without binder. The resulting chemiluminescent signal generated in the assays on each tray was detected using a pair of the detectors described above. One detector read the eight wells on the left side of the tray (Side A) and one detector read the eight wells on the right side of the tray (Side B). The results summarized in Table 10

TABLE 10

Anti-HBc Antibody Assay Using Matrix With And Without Binder

| | Matrix With Binder | | Matrix Without Binder | |
| --- | --- | --- | --- | --- |
| | mean* | S/N | mean* | S/N |
| | Side A | | Side A | |
| neg. (n = 8) | 1490 | | 792 | |
| Pos. (n = 8) | 32435 | 21.8 | 42447 | 53.6 |
| | Side B | | Side B | |
| neg. (n = 8) | 1660 | | 880 | |
| Pos. (n = 8) | 32700 | 19.7 | 41163 | 46.8 |

*mean = the mean chemiluminescent signal intensity (counts/6 sec.).

demonstrate that the binderless glass fiber matrix had not only substantially improved the sensitivity of the anti-HBc antibody assay by reducing background chemiluminescence, but also substantially enhanced the chemiluminescent signal generated in the assays of positive samples which significantly enhanced the signal-to-noise ratio (S/N).

Although the present invention has been described in terms of preferred embodiments, it is anticipated that various modifications and improvements will occur to those skilled in the art upon consideration of the present invention. Thus, shape, material and color of the vessel, material of the fibrous matrix, material and shape and number of layers of absorbant pad; angles of injection, shape of injectors, speed of injection, and type and composition of wash solution; and treatment of fibrous matrix to decrease non-specific binding can all be optimized by those skilled in the art. The device and method of this invention can be used to perform immunoassays for macromolecular antigens, viral and bacterial antigens and haptens. It can be extended to nucleic acid probes. Although the invention has been described using acridinium sulfonamide labeled tracers, it can be extended to other acridinium compounds or their analogs. Other kinds of chemiluminescence can be performed and detected using the device and method of this invention such as luminol type chemiluminescence or enzyme catalyzed dioxetane chemiluminescence. Further the device and method of this invention can be used with other detection methods and hence with other labels, such as front surface measurements using enzyme catalyzed substrate fluorescence or time resolved fluorescence, rare earth chelate labels or precipitated product immunoassays, and reflectance measurements.

While certain features and embodiments of the invention have been described in detail herein, it will be readily understood that the invention encompasses all enhancements and modifications within the scope and spirit of the following claims.

We claim:

1. An assay performing diagnostic device comprising:
    (a) a housing;
    (b) a well on the housing;
    (c) an opening in the well;
    (d) an absorbent pad supported by the housing and located underneath the opening;
    (e) a fibrous matrix supported by the housing and disposed between the opening in the well and the absorbent pad; and
    (f) a non-white pigmented light absorbing material located between the fibrous matrix and absorbent pad, wherein said light absorbing material absorbs light radiated from the absorbent pad.

2. An assay performing diagnostic device as defined in claim 1, wherein said light absorbing material comprises at least one of cellulose acetate containing carbon black and polycarbonate containing Irgalan black.

3. An assay performing diagnostic device as defined in claim 1, wherein the fibrous matrix is a binderless fibrous matrix.

4. An assay performing diagnostic device as defined in claim 1, wherein the fibrous matrix is a glass fibrous matrix.

5. An assay performing diagnostic device as defined in claim 1, wherein said light absorbing material is a non-white pigment disposed within or on the absorbent pad.

6. An assay performing diagnostic device as defined in claim 5 wherein the pigment has a light absorbance greater than a light absorbance of white material.

7. An assay performing diagnostic device for use with an analytical instrument including a detector for monitoring light, the assay performing diagnostic device comprising:
    (a) a housing;
    (b) a well on the housing;
    (c) an opening in the well;
    (d) an absorbent pad supported by the housing and located underneath the opening in the well;
    (e) a fibrous matrix supported by the housing and disposed between the absorbent pad and the opening in the well; and
    (f) a non-white pigmented light absorbing material located between the fibrous matrix and absorbent pad, wherein said light absorbing material absorbs light radiated from the absorbent pad to reduce light radiated to the detector of the analytical instrument.

8. An assay performing diagnostic device as defined in claim 7, wherein said light absorbing material is a non-white pigment disposed within or on the absorbent pad.

9. An assay performing diagnostic device as defined in claim 8, wherein the non-white pigment is at least one of carbon black and Irgalan black.

10. An assay performing diagnostic device comprising:
    (a) a housing;
    (b) a well disposed on the housing;
    (c) an opening in the well;
    (d) a fibrous matrix supported by the housing and located underneath the opening in the well; and
    (e) an absorbent pad supported by the housing and located underneath said fibrous matrix, said absorbent pad comprising a plurality of layers of absorbent material, wherein the upper most layer of absorbent material, adjacent to said fibrous matrix, contains a non-white pigment to absorb light radiated from the absorbent pad.

11. An assay performing diagnostic device for use with an analytical instrument including a detector for monitoring light, the assay performing diagnostic device comprising:
    (a) a housing;

(b) a well disposed on the housing;
(c) an opening in the well;
(d) a fibrous matrix supported by the housing and located underneath the opening in the well; and
(e) an absorbent pad supported by the housing and located underneath said fibrous matrix, said absorbent pad comprising a plurality of layers of absorbent material, wherein the upper most layer of absorbent material, adjacent to said fibrous matrix, contains a non-white pigment for absorbing light radiated from the absorbent pad to reduce light radiated to the detector of the analytical instrument.

* * * * *